(12) United States Patent
Lee et al.

(10) Patent No.: US 10,206,619 B1
(45) Date of Patent: Feb. 19, 2019

(54) DEVICE AND METHOD FOR MONITORING BODY HYDRATION

(71) Applicant: Maxim Integrated Products, Inc., San Jose, CA (US)

(72) Inventors: Janice C. Lee, Sunnyvale, CA (US); Nevzat A. Kestelli, San Jose, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 0 days.

(21) Appl. No.: 15/965,372

(22) Filed: Apr. 27, 2018

Related U.S. Application Data

(60) Provisional application No. 62/491,454, filed on Apr. 28, 2017.

(51) Int. Cl.
*A61B 5/00* (2006.01)

(52) U.S. Cl.
CPC .......... *A61B 5/4875* (2013.01); *A61B 5/0075* (2013.01); *A61B 5/7203* (2013.01); *A61B 5/681* (2013.01); *A61B 5/7435* (2013.01)

(58) Field of Classification Search
CPC .. A61B 5/4875; A61B 5/0086; G01N 33/246; G01N 21/33; G01J 3/42
See application file for complete search history.

(56) References Cited

U.S. PATENT DOCUMENTS

| | | | | |
|---|---|---|---|---|
| 4,823,008 A * | 4/1989 | Sturm | ................... | G01N 21/86 250/339.04 |
| 5,127,406 A * | 7/1992 | Yamaguchi | .......... | A61B 5/1455 422/73 |
| 6,266,546 B1 * | 7/2001 | Steuer | ................ | A61B 5/14535 600/316 |
| 8,357,090 B2 * | 1/2013 | Baker | .................. | A61B 5/0059 600/306 |
| 2002/0165439 A1 * | 11/2002 | Schmitt | ................ | A61B 5/0059 600/309 |
| 2008/0009690 A1 * | 1/2008 | Debreczeny | ....... | A61B 5/14551 600/336 |
| 2011/0102798 A1 * | 5/2011 | Holland | ............... | A01B 79/005 356/445 |
| 2012/0242979 A1 * | 9/2012 | Nishida | .............. | A61B 5/14532 356/51 |
| 2013/0073220 A1 * | 3/2013 | Nishida | ................ | G01N 21/274 702/25 |

(Continued)

*Primary Examiner* — Maurice Smith

(74) *Attorney, Agent, or Firm* — Kevin E. West; Advent, LLP

(57) ABSTRACT

A device configured to furnish hydration monitoring employs a method using multiple different wavelengths of light transmitted into a human body part, each wavelength being input at a given respective input intensity. Respective output intensities of respective ones of the multiple wavelengths can be measured, upon transmission thereof through the human body part. The corresponding input intensity and the corresponding output intensity for the respective ones of the transmitted wavelengths can be used along with a form of an equation for the Beer-Lambert law to calculate a concentration-related slope, the concentration-related slope being proportional to the relative concentration of water in the human body part at a given time. A hydration-level output indicative of a level of hydration can then be generated based on the concentration-related slope.

20 Claims, 23 Drawing Sheets

(56) References Cited

U.S. PATENT DOCUMENTS

| | | |
|---|---|---|
| 2015/0088002 A1 | 3/2015 | Podhajsky et al. |
| 2015/0313541 A1 | 11/2015 | Rymut |
| 2017/0014035 A1* | 1/2017 | Newberry .......... A61B 5/02055 |
| 2017/0319131 A1 | 11/2017 | Da Silveira et al. |

* cited by examiner

Running time (~1.5 hours)

DEVICE AND METHOD FOR MONITORING BODY HYDRATION

BACKGROUND

It may be desirable to monitor body hydration of persons, particularly athletes and/or elderly people. One past approach for measuring body and/or skin hydration employs spectral measurement in which a spectrometer, a light source, and filters are used. Another past approach employs a light source to perform reflection measurement of the tissues, relying on the input of presumed optical properties of tissues to make the necessary calculations.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Overview

Figure 1A:
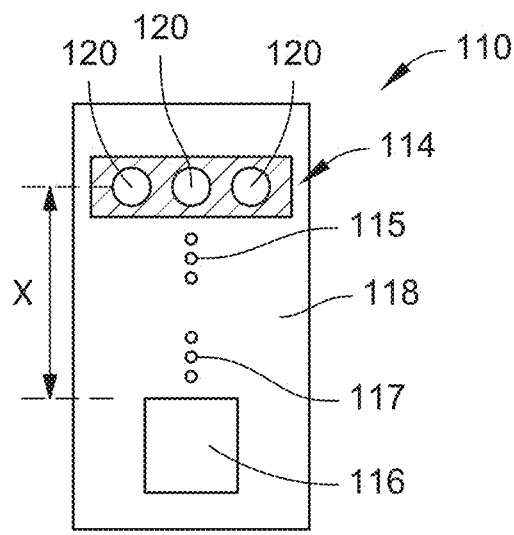
FIG. 1A is a top, diagrammatic view of an embodiment of a hydration monitor, in accordance with an example implementation of the present disclosure.

A device (e.g., a mobile device, a wearable monitor, and so forth) and the related methods for using the device can provide for a non-invasive optical technique using multi-wavelength light sources included in a light module, such as a light-emitting diode module having light-emitting diodes and/or a broadband light-emitting diode (LED) in conjunction with one or more light sensors (e.g., photodiodes) to measure body hydration (water concentration in body tissues) for wearable applications and other applications. Examples of a broadband LED includes but is not limited to one or more broadband LED's that emit broadband infrared light (e.g., in a range from about 650 to about 1050 nanometers (nm)). The device may be placed (e.g., worn, donned) anywhere it can be coupled to the skin or other tissue of a body (e.g., a portion of the human body, such as a wrist, a calf, the torso, etc.) The method may be attractive, for example, because (1) it is easy to implement, (2) it can reduce inaccuracy due to unknown optical properties of tissues, (3) it can reduce inaccuracy due to a user's motion, and/or, in some embodiments, (4) it gives robust performance by accounting for lipid and/or melanin content variation in a diverse population.

In some embodiments, the methods can correlate an optical signal, upon transmission through tissue (e.g., within an arm or a leg upon which the device is donned), to the absorption coefficient of water at multiple (e.g., two or more) wavelengths, by employing the Beer-Lambert Law, a simplified version of which is expressed here:

$$I_{out} = I_{in} e^{-(C\mu_a L) + G}$$ Eqn. 1

The Beer-Lambert Law relates the transmitted intensity $I_{out}$ to the incident intensity $I_{in}$ in a medium. The intensity drops exponentially with the concentration C [normalized to unity] and absorption coefficient $\mu_a$ [e.g., $cm^{-1}$ or $in^{-1}$] of an absorbing element. L is the path length [e.g., cm or in] traveled by the light. Path length L may not be a linear path in the tissue (e.g., the path the light travels from the light emitter to the light sensor). For example, the path length L can be non-linear and/or arcuate. G is a factor that captures a contribution due to scattering caused by tissues. In the case of a hydration sensor, the absorbing element of interest is water, and the concentration C of water is the unknown to be measured. Absorption coefficient $\mu_a$ of water depends on wavelength, and such absorption coefficients are publicized in the literature, e.g., in the form of look-up tables (e.g., the values of which can be programmed into a related controller for calculating the water concentration C and/or stored in a memory or other data store that can be accessed by the controller). It is noted that the arrow L is used here only to depict the concept of the path length, and by no means is meant to represent the actual path length traveled by the light (e.g., typically, the light may not travel a straight path as it travels through the tissue).

The transmitted signal may be plotted against the water absorption coefficient in a linear regression plot. The slope of the linear fit, relative to any of the example embodiments, can provide information about the hydration level. Such "slope methods" can display, for example, such benefits as scattering of light due to tissues can be hard to characterize and/or can vary largely across a population, and such scattering is generally included in the y-intercept of the plot, not affecting the slope (i.e., the hydration result); user motion, which tends to have common effect on signals for all wavelength channels (e.g., by affecting the optical coupling between the light emitting diodes (LEDs) and the tissues, the light sensors and the tissues, or both), is another factor that can be lumped into the y-intercept of the related equation, generally leaving the slope relatively intact, and reducing motion error; and a quality metric is provided by the goodness of fit, $R^2$, as associated with a given data plot.

Example Implementations

Referring now generally to FIGS. 1A, 1B, 1C, 1D, and 3, embodiments of a device 100 (FIG. 3) (e.g., a mobile device, a wearable device or a carried device such as a wristwatch device, a strap band device (heart rate monitor), a mobile phone, a smartphone, or the like) are described which can incorporate a hydration monitor 110 (FIGS. 1A and 1B) and a controller 112 (FIG. 3) in accordance with the present disclosure. In some examples, the hydration monitor 110 may be included in a medical device or a clinical device configured to measure and/or monitor hydration content and/or a hydration trend in tissue.

FIG. 1A illustrates an example hydration monitor 110. As shown, the hydration monitor 110 includes one or more light-emitting diode (LED) modules 114 and one or more light sensors (e.g., photodiodes or other device configured to convert incident light into an electrical signal) 116 carried on one or more substrates 118 (e.g., a printed circuit board (PCB), a flexible PCB, an integrated circuit (IC), an application specific integrated, circuit (ASIC), or another electronics-carrying member), with one such substrate 118 being shown. Substrate 118 may be mounted, positioned or otherwise incorporated into a chassis, housing or other structure. FIG. 1A depicts a hydration monitor 110 having one light-emitting diode module 114 and one light sensor 116. However, the hydration monitor 110 may include multiple light-emitting diode modules 114 as denoted by 115 and/or multiple light sensors 116 as denoted by 117. In the embodiment shown in FIG. 1A, the light-emitting diode module 114 (each of the light-emitting diode modules 114 where multiple such modules 114 are provided) includes at least two (2) light-emitting diodes 120, wherein respective ones of the light-emitting diodes 120 have a separate/distinct wavelength (e.g., three (3) light-emitting diodes 120 furnishing three (3) separate/distinct wavelengths, or two (2) light-emitting diodes 120 furnishing two (2) separate/distinct wavelengths). For example, cost of the device 110 and/or the led module 114 may be reduced and area of the device 110 and/or led module 114 may be reduced by using two (2) LED's instead of three (3) LED's. However, in some embodiments, the light-emitting diode module 114 may include one or more broadband light-emitting diodes (e.g., a multi-wavelength light-emitting diode in which multiple (e.g., three (3) or more) different wavelengths are simultaneously generated). The one or more light-emitting diode modules 114 and the one or more light sensors 116 may be operatively connected (e.g., via a wired or wireless connection 113) with a controller 112 shown in FIG. 3. For example, the signal Sin depicted in FIG. 2 may be generated by controller 112 (e.g., a signal having a magnitude, a duty cycle, etc.) and communicated to the LED module(s) via connection 113. Further, signal Sout depicted in FIG. 2 may be a signal received by controller 112 via connection 113 (e.g., an output signal from a photodiode that is indicative of the intensity of light Iout incident on the light sensor 116). The controller 112, as shown in FIG. 3, may further include a processor 142, a memory 144, and a communications interface 146. The hydration monitor 110 and the controller 112 may be powered by any suitable source of power (e.g., a rechargeable battery or the like).

Figure 1B:
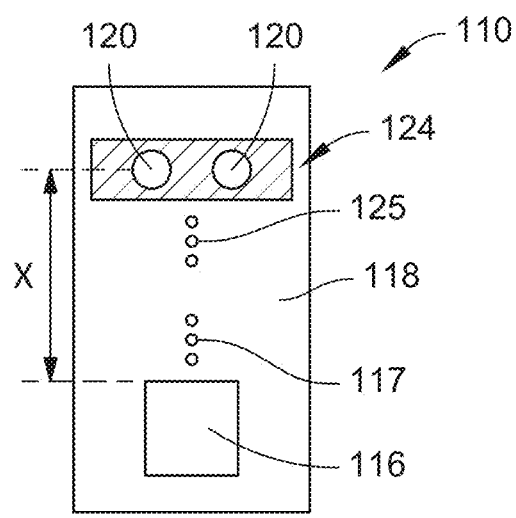
FIG. 1B is a top, diagrammatic view of another embodiment of a hydration monitor, in accordance with an example implementation of the present disclosure.

FIG. 1B illustrates another example hydration monitor 110. As shown, the hydration monitor 110 includes one or more light-emitting diode (LED) modules 124 and one or more light sensors (e.g., photodiodes) 116 carried on one or more substrates 118 (e.g., a printed circuit board (PCB), a flexible PCB, or another electronics-carrying member), with one such substrate 118 being shown. FIG. 1B depicts a hydration monitor 110 having one light-emitting diode module 124 and one light sensor 116. However, the hydration monitor 110 may include multiple light-emitting diode modules 124 as denoted by 125 and/or multiple light sensors 116 as denoted by 117. In the embodiment shown in FIG. 1B, the light-emitting diode module 124 (each of the light-emitting diode modules 124 where multiple such modules 114 are provided) includes two (2) light-emitting diodes 120, wherein respective ones of the light-emitting diodes 120 have a separate/distinct wavelength (i.e., two (2) light-emitting diodes 120 furnishing two (2) separate/distinct wavelengths). However, in some embodiments, the light-emitting diode module 124 may include one or more broadband light-emitting diodes (e.g., a multi-wavelength light-emitting diode in which multiple (e.g., two (2) or more) different wavelengths are simultaneously generated). The one or more light-emitting diode modules 124 and the one or more light sensors 116 may be operatively connected (e.g., via a wired or wireless connection 113) with the controller 112 shown in FIG. 3. The controller 112, as shown in FIG. 3, may further include a processor 142, a memory 144, and a communications interface 146. The hydration monitor 110 and the controller 112 may be powered by any suitable source of power (e.g., a rechargeable battery or the like).

Figure 1C:
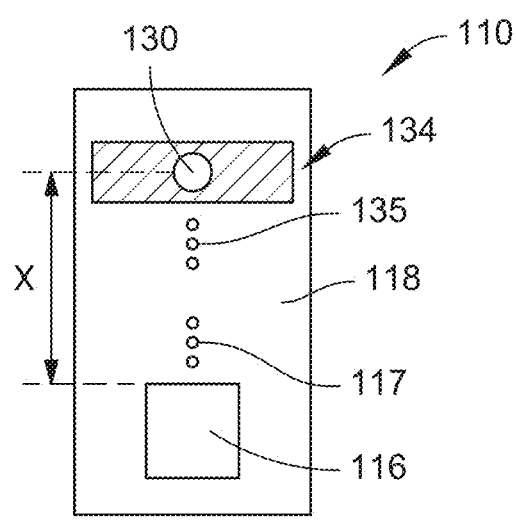
FIG. 1C is a top, diagrammatic view of another embodiment of a hydration monitor, in accordance with an example implementation of the present disclosure.

FIG. 1C illustrates a further example hydration monitor 110. As shown, the hydration monitor 110 includes one or more light-emitting diode (LED) modules 134 and one or more light sensors (e.g., photodiodes) 116 carried on one or more substrates 118 (e.g., a printed circuit board (PCB), a flexible PCB, or another electronics-carrying member), with one such substrate 118 being shown. FIG. 1C depicts a hydration monitor 110 having one light-emitting diode module 134 and one light sensor 116. However, the hydration monitor 110 may include multiple light-emitting diode modules 134 as denoted by 135 and/or multiple light sensors 116 as denoted by 117. In the embodiment shown in FIG. 1C, the light-emitting diode module 134 (each of the light-emitting diode modules 134 where multiple such modules 134 are provided) includes one or more broadband light-emitting diodes 130 (e.g., a multi-wavelength light-emitting diode in which multiple (e.g., two, three, or more) different wavelengths are simultaneously generated). The one or more light-emitting diode modules 134 and the one or more light sensors 116 may be operatively connected (e.g., via a wired or wireless connection 113) with the controller 112 shown in FIG. 3. The controller 112, as shown in FIG. 3, may further include a processor 142, a memory 144, and a communications interface 146. The hydration monitor 110 and the controller 112 may be powered by any suitable source of power (e.g., a rechargeable battery or the like).

Figure 1D:
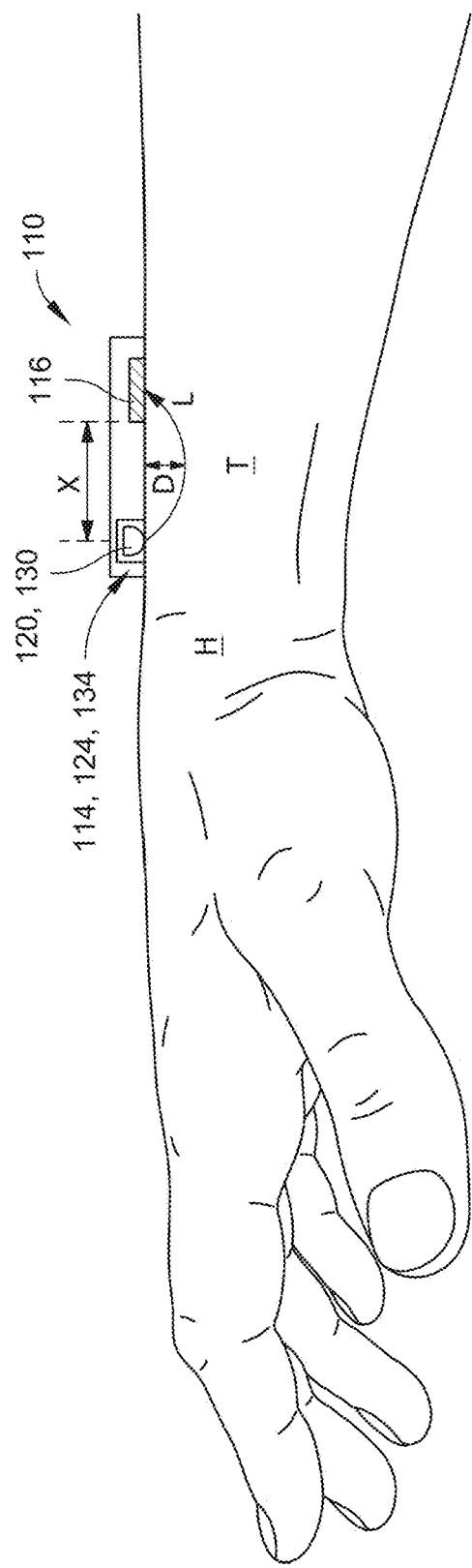
FIG. 1D is a side, diagrammatic view of a hydration monitor such as the hydration monitors shown in FIGS. 1A, 1B, and 1C, mounted on tissue of a human body.

As shown in FIG. 1D, the light-emitting diode modules 114, 124, 134 (one light-emitting diode module 114, 124, 134 is shown) can be positioned proximate a human body part ("H") (e.g., a wrist, arm, chest, calf, etc.) without interference from any intervening clothing, such that the wavelengths of light generated by light-emitting diodes 120, 130 of the light-emitting diode module 114, 124, 134 may penetrate deep (e.g., below skin level) within the tissue ("T") of the human body part H. In some embodiments, the light-emitting diode module 114, 124, 134 may be in direct contact with the human body part H to maximize transmission of emitted light into the tissue T of the human body part H (e.g., minimizing opportunities for reflection by the skin). In some embodiments, at least a portion of the wavelengths of light generated by the light-emitting diode module 114 may be in the infrared (IR) range (e.g., light having wavelengths of approximately 800 nm-2.5 μm), as the infrared range is where water absorption dominates. In one embodiment, IR light having the wavelengths of 880 nm, 940 nm, and 970 nm can be chosen. However, it should be understood that light having other wavelengths may be selected. Each of the wavelengths of light generated by the light-emitting diode module 114, 124, 134 can have a respective input (e.g., entry into body) intensity (e.g., luminous intensity) associated therewith. In some embodiments, the input intensity may be measured in terms of, for example, the metric unit for luminous intensity, which is the candela (cd). In other embodiments, the intensity of a given wavelength may be deemed proportional to the power and/or the current associated therewith. For example, the input intensity may be determined by an electrical signal (e.g., voltage, current or both) applied to one or more LED's in the light-emitting diode module (114, 124, 134) and a magnitude of the electrical signal may be modulated and/or have its duty cycle controlled to emit light at the desired luminous intensity.

Figure 1E:
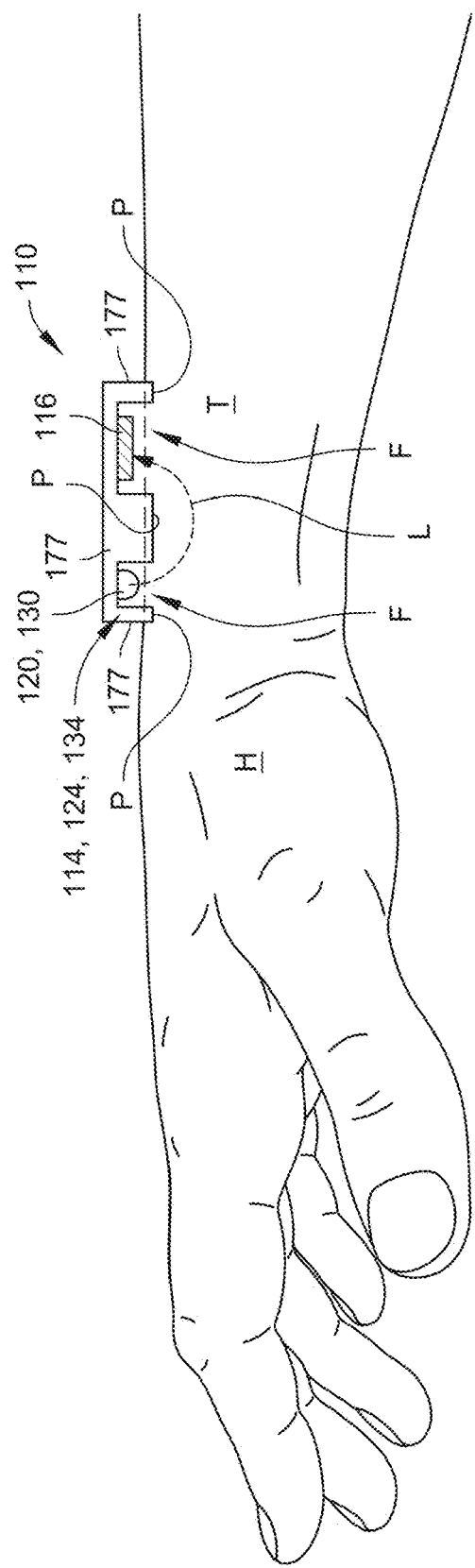
FIG. 1E is a side, diagrammatic view of a hydration monitor including a baffle and mounted on tissue of a human body.

The light-emitting diode module 114, 124, 134 and the one or more light sensors 116 can be separated from one another on the substrate 118 by a distance ("X"). In the embodiments illustrated, the distance X is measured from the center of the respective light-emitting diodes 120, 130 and the closest edge of the light sensor (photodiode) 116. However, the distance X may be measured between other reference points in FIGS. 1A-1C (e.g., substantially from the center of the LED to the center of the light sensor). Light is capable of propagating from the light-emitting diode module 114, 124, 134, penetrating to a depth ("D") within the tissues T of the human body part, and traveling an overall path length ("L") to reach a given light sensor 116. The overall path length L is determined, at least in part, by scattering properties of the surrounding tissues. The depth D may vary along the path length X. The hydration measurement of the tissues is a function of the overall path length L, and this function is to be described in upcoming paragraphs. It is to be further understood that, due to light transmission and scattering properties within the tissue T associated with the human body part, only a portion of the wavelengths generated by the light-emitting diode module 114, 124, 134 may even reach a given light sensor 116. To help ensure that wavelengths reach a given light sensor 116 by transmission through deep penetration within the tissues T of the human body part H and not simply, for example, via reflection off the skin surface, scattering along the skin surface, and/or direct transmission through the air, the distance X may have a minimum distance associated therewith. In some embodiments, the minimum distance of X can be 1 cm, for example. In some embodiments, having direct contact of the given light sensor 116 with the human body part can also aid in ensuring that primarily, if not only, deep-penetrating wavelengths of light can reach the light sensor 116. In some embodiments, one or more light baffles may also be added to block/intercept/attenuate undesired surface reflection from reaching the light sensor(s). For example, in FIG. 1E, the hydration monitor 110 may include at least one structure configured as a light baffle 177. A portion of the baffle 177 may be disposed substantially flush with a surface of the tissue T as denoted by dashed line F, and/or a portion of the baffle 177 may be positioned inward of the surface of the tissue T (e.g., pressed slightly inward of the surface of the tissue T) as denoted by P. For example, one or more of the baffles 177 may be configured to prevent extraneous light from the environment (e.g., sunlight, artificial light) from reaching one or more of the light sensors 116. As another example, one or more of the baffles 177 may be configured to prevent or substantially attenuate light being emitted from one or more LED's (120, 130) in one or more LED modules (114, 124, 134) from being incident on the light sensor 116 on a path other than that depicted by path length L to ensure a substantial portion of the emitted light travels subcutaneously through tissue T (e.g., at depth D in FIG. 1D). Baffle 177 may be made from a material that is opaque or substantially opaque to the light being emitted by the LED's (120, 130), ambient light, or both, for example. LED modules (114, 124, 134) and light sensor(s) 116 may be separated by a distance (not shown), such as the distance X in FIGS. 1A-1D, for example.

Figure 2:
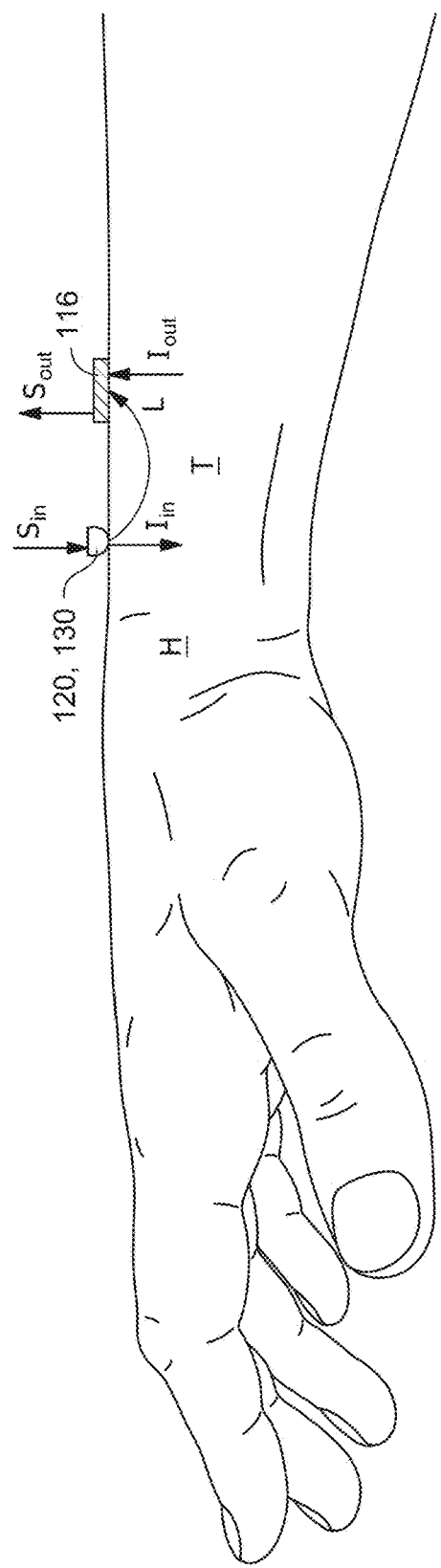
FIG. 2 is a side, diagrammatic view illustrating operation of the hydration monitors shown in FIGS. 1A, 1B, 1C, 1D and 1E in accordance with the Beer-Lambert law.
Figure 3:
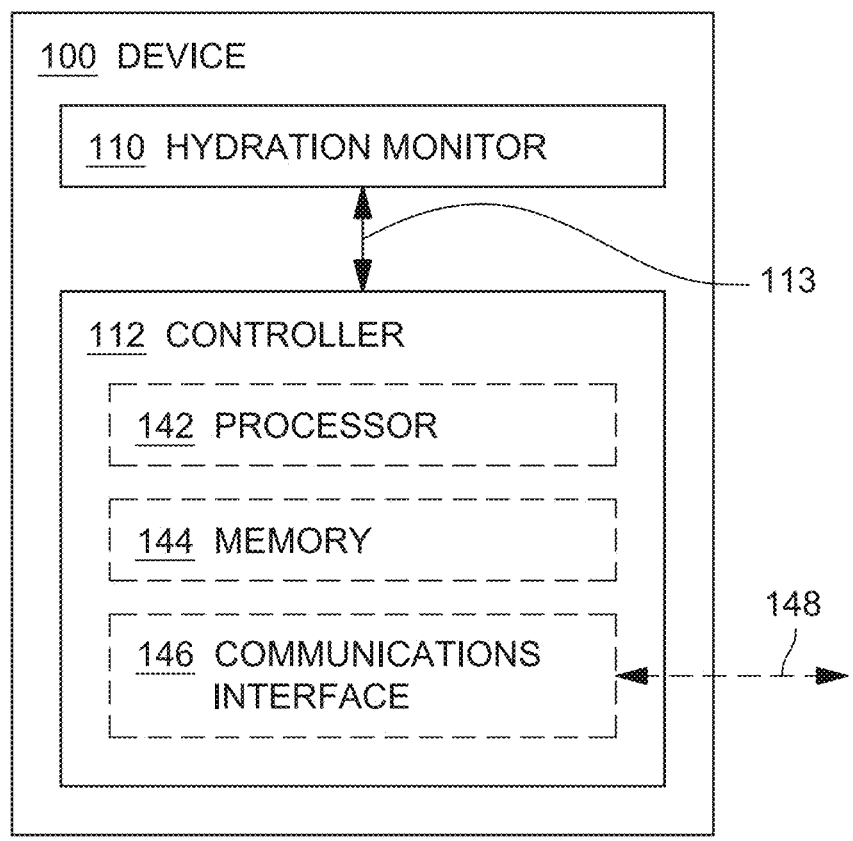
FIG. 3 is a diagrammatic view of a device incorporating a hydration monitor such as the hydration monitors shown in FIGS. 1A, 1B, 1C, 1D and 1E in accordance with an example implementation of the present disclosure.

FIG. 2 illustrates operation of the hydration monitors 110 shown in FIGS. 1A, 1B, 1C, and 1D in accordance with the Beer-Lambert law (Eqn. 1). As shown in FIG. 2, the Beer-Lambert law (Eqn. 1) relates a transmitted intensity $I_{out}$, which is detected by the light sensors 116 to produce an output signal Sour, to an incident intensity $I_{in}$ transmitted into the tissue T by the light-emitting diodes 120, 130 in response to an input signal $S_{in}$. The intensity $I_{out}$ drops exponentially with the concentration C [normalized to unity] and absorption coefficient $\mu_a$ of an absorbing element. L is the path length traveled by the light emitted by the light-emitting diodes 120, 130. G is a factor that captures a contribution due to scattering caused by tissues. In the case of a hydration sensor, the absorbing element of interest is water, and the concentration C of water is the unknown to be measured.

FIG. 3 illustrates, in a diagrammatic form, a device 100, which can incorporate a hydration monitor 110 and a controller 112. The controller 112, as shown in FIG. 3, may further include a processor 142, a memory 144, and a communications interface 146. In some embodiments (although not shown), the controller 112 can be carried by (e.g., mounted upon) the substrate 118, along with the elements of the hydration monitor 110. In some embodiments, the controller 112 can be a separate device, carried apart from the hydration monitor 110. The hydration monitor 110 and the controller 112 may be powered by any suitable source (e.g., a rechargeable battery). In some embodiments, the device 100 and, particularly, the hydration monitor 110 can be placed in contact with a given human body part H. For example, the device 100 may be a wearable device (e.g., wristwatch-style; one in which a releasable strap is included as part of the device 100) configured to be connected to a given human body part H and, in some embodiments, capable of ongoing monitoring over a period of time (e.g., while device is charged and/or activated). In a further example, the device 100 may be configured to be brought into contact to a human body part H without necessarily being worn thereon. In this latter example, the device 100 may, in one embodiment, be used for a "point-in-time" measurement of a person's hydration level, and such a device 100 could be in the form of, e.g., a portable medical monitoring device, a smart phone, a tablet, or another similar device. It is however, understood that, even with this latter device, the device 100 may be converted to a wearable version by using, e.g., a releasable strap or another auxiliary mounting unit in conjunction with the device 100.

The device 100 can include a controller 112. The device 100, including some or all of its components, can operate under computer and/or processor control. For example, a processor 142 can be included with or in device 100 and/or controller 112 to control the components and functions of the device 100 described herein using software, firmware, hardware (e.g., fixed logic circuitry), or a combination thereof. The terms "controller," "functionality," "service," and "logic" as used herein generally represent software, firmware, hardware, or a combination of software, firmware, or hardware in conjunction with controlling the device 100. In the case of a software implementation, the module, functionality, or logic represents program code (e.g., algorithms embodied in a non-transitory computer readable medium) that performs specified tasks when executed on a processor (e.g., central processing unit (CPU) or CPUs). The program code can be stored in one or more non-transitory computer-readable memory devices or media (e.g., internal memory and/or one or more tangible media), and so on. For example, memory may include but is not limited to volatile memory, non-volatile memory, Flash memory, SRAM, DRAM, RAM and ROM. The structures, functions, approaches, and techniques described herein can be implemented on a variety of commercial computing platforms having a variety of processors.

The processor 142 provides processing functionality for at least the device 100/controller 112 and can include any number of processors, micro-controllers, digital signal processors (DSP), circuitry, field programmable gate array (FPGA) or other processing systems, and resident or external memory for storing data, executable code, and other information accessed or generated by the device 100/controller 112. The processor 142 can execute one or more software programs embodied in a non-transitory computer readable medium that implement techniques described herein. The processor 142 is not limited by the materials from which it is formed or the processing mechanisms employed therein and, as such, can be implemented via semiconductor(s) and/or transistors (e.g., using electronic integrated circuit (IC) components), and so forth.

The controller 112 may include a memory 144 (e.g., Flash memory, RAM, SRAM, DRAM, ROM, etc.). The memory 144 can be an example of tangible, computer-readable storage medium that provides storage functionality to store various data and or program code associated with operation of the device 100/controller 112, such as software programs and/or code segments, or other data to instruct the processor 142, and possibly other components of the device 100/controller 112, to perform the functionality described herein (e.g., store data associated with and/or used to compute equations described herein). Thus, the memory 144 can store data, such as a program of instructions for operating the device 100 (including its components), and so forth. It should be noted that while a single memory 144 is described, a wide variety of types and combinations of memory (e.g., tangible, non-transitory memory) can be employed. The memory 144 can be integral with the processor 142, can comprise stand-alone memory, or can be a combination of both.

Some examples of the memory 144 can include removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the device 100 and/or the memory 144 can include removable integrated circuit card (ICC) memory, such as memory provided by a subscriber identity module (SIM) card, a universal subscriber identity module (USIM) card, a universal integrated circuit card (UICC), and so on.

The controller 112 may include a communications interface 146. The communications interface 146 can be operatively configured to communicate with components of the device 100. For example, the communications interface 146 can be configured to transmit data for storage in the device 100, retrieve data from storage in the device 100, and so forth. The communications interface 146 can also be communicatively coupled with the processor 142 to facilitate data transfer between components of the device 100 and the processor 142 (e.g., for communicating inputs to the processor 142 received from a device communicatively coupled with the device 100/controller 112). It should be noted that while the communications interface 146 is described as a component of a device 100/controller 112, one or more components of the communications interface 146 can be implemented as external components communicatively coupled to the device 100 via a wired and/or wireless connection. The device 100 can also include and/or connect to one or more input/output (I/O) devices (e.g., via the communications interface 146), such as a display, a mouse, a touchpad, a touchscreen, a keyboard, a microphone (e.g., for voice commands) and so on. In some examples, the communications interface 146 may include or be in communication with a display (not shown) configured to visually display data representing water concentration in tissue, body hydration trend, tissue hydration level, or other data related to hydration. The information being displayed on the display may include but is not limited to numbers, graphics, icons, images or the like.

The communications interface 146 and/or the processor 142 can be configured to communicate 148 with a variety of different networks (e.g., using one or more communications protocols), such as a wide-area cellular telephone network, such as a cellular network, a 3G cellular network, a 4G cellular network, or a global system for mobile communications (GSM) network; a wireless computer communications network, such as a WiFi network (e.g., a wireless local area network (WLAN) operated using IEEE 802.11 network standards); an ad-hoc wireless network, an intranet; the Internet; a wide area network (WAN); a local area network (LAN); a personal area network (PAN) (e.g., a wireless personal area network (WPAN) operated using IEEE 802.15 network standards); a public telephone network; an extranet; an intranet; Bluetooth; Bluetooth LE; NFC; Zigbee; Ad-Hoc WiFi; Software Defined Radio, and so on. However, this list is provided by way of example only and is not meant to limit the present disclosure. Further, the communications interface 146 can be configured to communicate with a single network or multiple networks across different access points. In a specific embodiment, a communications interface 146 can transmit information from the controller 112 to an external device (e.g., a cell phone, a computer connected to a WiFi network, cloud storage, etc.). In another specific embodiment, a communications interface 146 can receive information from an external device (e.g., a cell phone, a computer connected to a WiFi network, cloud storage, etc.). In another specific embodiment, a communications interface 146 can transmit and/or receive information from an external device via a Bluetooth connection (i.e., a wireless technology standard for exchanging data over short distances (using short-wavelength UHF radio waves in the ISM band from 2.4 to 2.485 GHz) from fixed and mobile devices).

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Example Methods

In general, there may be at least three example methods based on the Beer-Lambert law that can be used in conjunction with the device 100 and/or the hydration monitor 110 to extract tissue hydration level (water concentration) in, e.g., a given human body part H. The essence of the methods fundamentally correlates the transmitted optical signal to the absorption coefficient of water at multiple wavelengths. The transmitted signal is plotted against the water absorption coefficient in a linear regression plot. The slope of the linear fit provides information about the hydration level. Subsequently, data representing the hydration level may be communicated or otherwise generated as output from the device 100 (e.g., using the communications interface 146).

Figure 4:
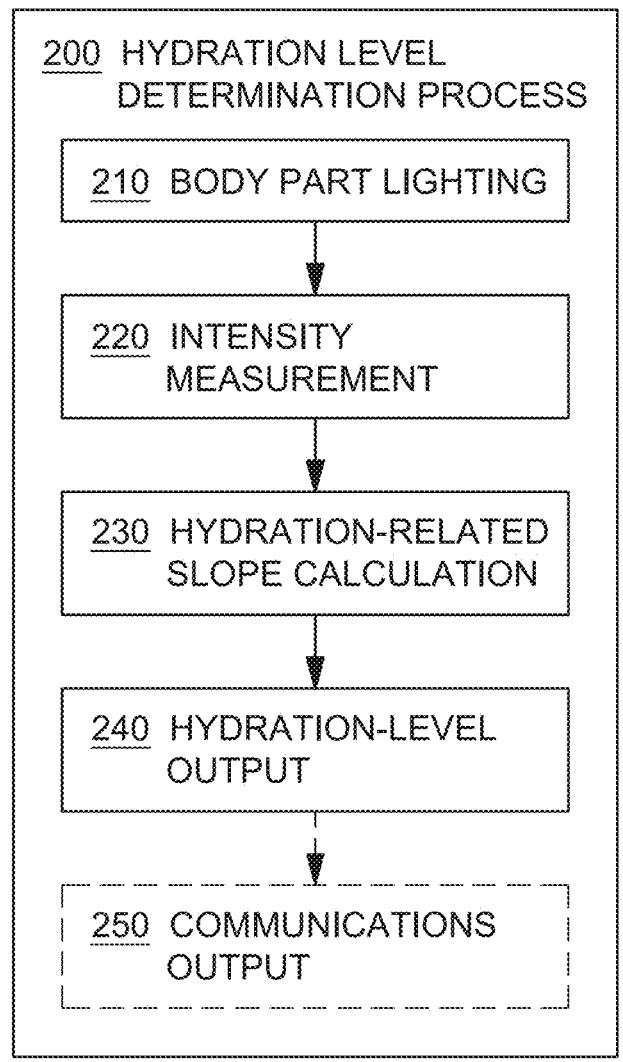
FIG. 4 is a block diagram outlining a method of extracting water concentration in tissue in accordance with an example implementation of the present disclosure.

FIG. 4 outlines a base process 200 of extracting (e.g., calculating, determining) data representing water concentration/hydration level, in conjunction with the Beer-Lambert law and using the device 100 and/or the hydration monitor 110. It is to be understood that the base process 200 is generally applicable to the three example embodiments to be discussed herein. First, per a body-part-lighting step 210, multiple wavelengths of light can be input (e.g., emitted via light-emitting diode module 114) into a human body part H, each wavelength being input at a given respective input intensity. Then, in an intensity-measurement step 220, corresponding output intensities of respective ones of the multiple wavelengths are measured (e.g., light received at a given light sensor 116), upon transmission thereof through the human body part. In a hydration-related-slope-calculation step 230 (e.g., performed by the controller 112 or other processor), the corresponding input intensity and the corresponding output intensity for the respective ones of the transmitted wavelengths are used, along with a form of an equation for the Beer-Lambert law, to calculate data representing a concentration-related slope, the concentration-related slope being proportional to the relative concentration of water in the human body part at a given time. Per a hydration-level-output step 240, data representing a hydration-level output indicative of a level of hydration based on the concentrated-related slope is generated (e.g., via the controller 112 and/or elements operatively associated therewith). It is to be understood that, in some embodiments, the hydration-level output can be a single, "point-in-time" reading or, in other embodiments, can incorporate a series of such measurements taken over a period of time (e.g., steps 210-240 repeated over a period of time to create a multi-point data set). Where a series of measurements are taken, in some embodiments, such data can be presented as a plot versus time; data provided as an average with or without a standard deviation; and/or other known means of displaying and/or analyzing data). In some embodiments, the hydration-level output (whether based on a "point-in-time" or a period of time) may be in the form, for example, an audio alert or message, a simple color-coded message (e.g., red (hydration needed immediately); yellow (hydration needed soon); and green (hydration sufficient)), a haptic indicator (e.g., a vibration pattern indicative of hydration-level), a percentage hydration level, and/or another easy-to-understand display (e.g., any quickly and/or readily understood message format). Per a communications output step 250, the hydration level output may be output as data or other signal (e.g., by controller 112, processor 142 or communications interface 146) as data that may be stored in memory, presented on a display, generate a sound or generate a haptic event, etc.

With respect to the first example method, the following equation with respect to the Beer-Lambert law may be used:

$$\underbrace{Ln\left(\frac{I_{out,i}}{I_{in,i}}\right)}_{y} = \underbrace{\overbrace{(-CL)}^{slope}\underbrace{\mu_a}_{x} + \overbrace{(G)}^{intercept}}\quad\text{Eqn. 2}$$

where the subscript i denotes the index for the wavelength used. Per Eqn. 2, the slope, as it incorporates both the concentration C and path length L terms, may be considered proportional to the concentration of water in a given human body part H. In some embodiments, it can be sufficient for the slope to be proportional to the concentration C, as a relative level of hydration may still be ascertained therefrom.

Figure 5:
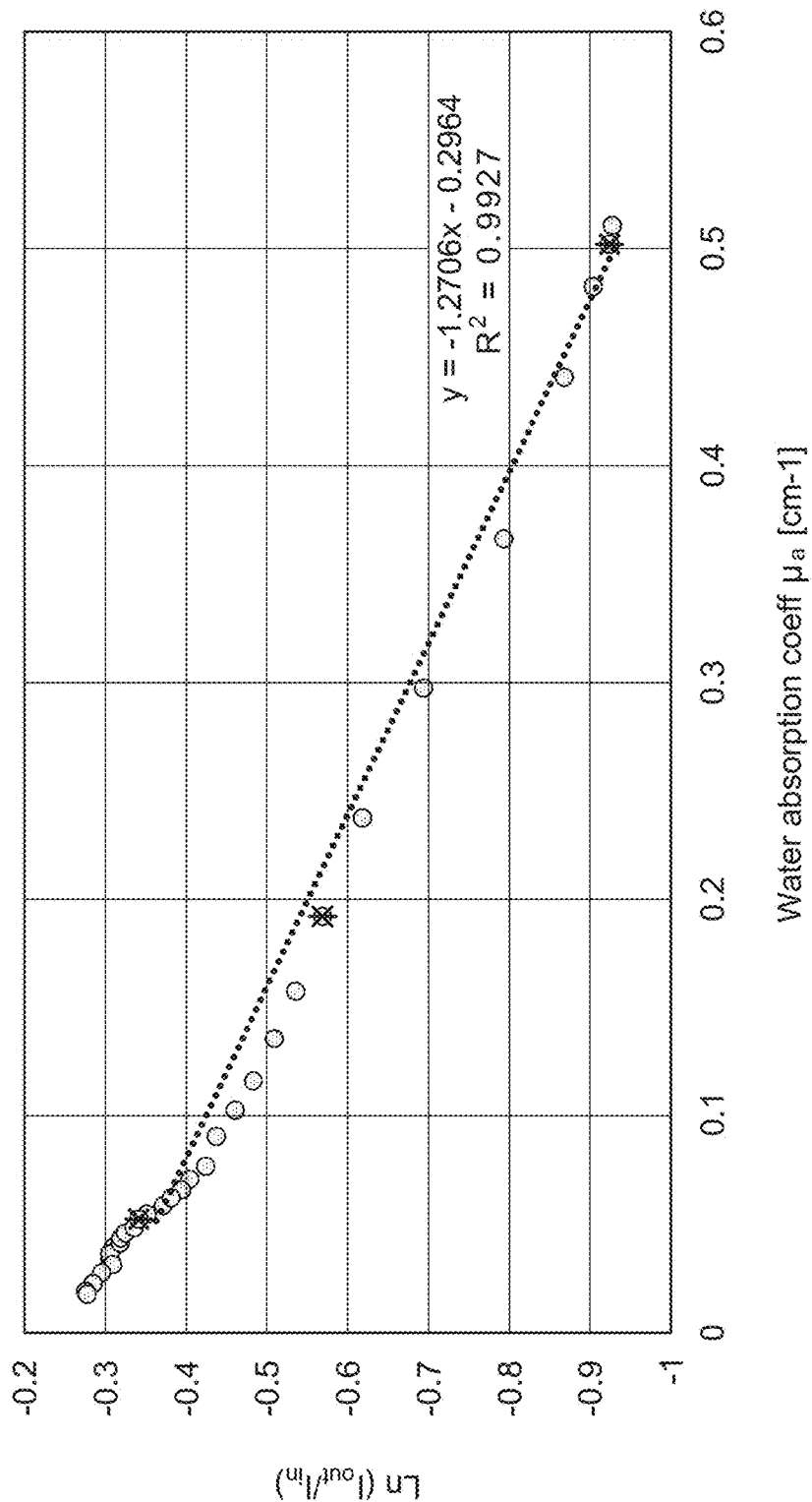
FIG. 5 is a graph of transmitted intensity versus water absorption coefficient measured using a broadband light, in accordance with an example implementation of the present disclosure.

FIG. 5 is a graph of transmitted intensity versus water absorption coefficient measured using a broadband light, as per the first example method. A subset of data constituting three wavelengths denoted with an asterisk "*" was selected to illustrate the expected results if three discrete LED wavelengths (e.g., two or three LED's with each LED emitting light at a wavelength being different than the other LED's) were used instead of broadband light (e.g., light emitted by a broadband LED or broadband LED's). A linear regression was then applied to the data subset of the three wavelengths to extract the slope, y-intercept, and R-squared of the fit. Experimental data showing $Ln(I_{out}/I_{in})$ vs. absorption coefficient $\mu_a$ of water over wavelength range of 800-975 nm. Data were measured with a broadband light of an input intensity $I_{in}$ that was in direct contact with the wrist as the selected human body part H. An output signal corresponding to the output intensity $I_{out}$ was collected 1 cm (e.g., X=1 cm) away the inputted broadband light. Direct contact with the wrist and the separation distance X of 1 cm helped to ensure that light penetrates deep into the tissues, rather than being reflected off the skin surface and/or scattered along the skin surface. A different separation distance (i.e., separation distance X) can also be used, providing both deep penetration and signal-to-noise requirements are still met. In addition to a broadband light-emitting diode, multiple light-emitting diodes, each respectively with a characteristic wavelength, were also used in generating the graph shown in FIG. 5. A linear fit was performed for three data points denoted by an asterisk "*" (i.e., a case when i=3) associated with wavelengths of 880 nm, 940 nm, and 970 nm (e.g., three wavelengths chosen to be within the infrared spectrum) to illustrate a possible implementation of multiple light-emitting diodes as part of the first example method. As seen from the linear fitting shown in FIG. 5, for the example provided, the linear fit associated with the broadband light-emitting diode and the linear fit associated with the multiple light-emitting diodes that are substantially matched up. From the slope of the linear fit, one can extract the water concentration C and/or a term proportional to the water concentration C. The goodness of fit $R^2$ associated with a given linear fit can serve as a quality metric for the accuracy of the extracted water or hydration level.

To measure and characterize the intensity $I_{In}$ of each wavelength may not be practical in a mass production setting and can also be deemed to be unnecessary. Only the relative intensity of the wavelengths need to be determined, and such relative intensity can be characterized using a simple reflective method or similar method that can be easily implement in a mass production setting. Assume the intensity for each wavelength as below:

$$I_{in1}=r_1 I_{in,same}$$

$$I_{in2}=r_2 I_{in,same}$$

$$I_{in3}=r_3 I_{in,same}$$

Then Eqn. 2 can be re-written to explicitly show how the output intensity $I_{out}$ is scaled by the ratio r before being plotted as y-axis:

$$\underbrace{Ln\left(\frac{I_{out,i}}{r_i}\right)}_{y} = \overbrace{(-CL)}^{slope}\underbrace{\mu_a}_{x} + \overbrace{(Ln(I_{in,same})+G)}^{intercept}\quad\text{Eqn. 3}$$

Note the setting with all input intensities being equal (when $r_1=r_2=r_3$) can also be used. Additionally, the power requirement can, in some embodiments, be pre-conditioned during factory trimming/calibration (e.g., of the LED's and/or their respective drive circuitry).

During calibration (e.g., time=0) of the third method, bias current for each light-emitting diode is swept to determine the setting where the detected power $I_{out,\,equal}$ is found to be equal. This can be done with automatic gain control circuitry (AGC) or by software commands. Mathematically, the input required can be written as:

$$I_{in}=I_{out,equal}e^{+(C_w\mu_w L_w)}e^{+(C_l\mu_l L_l)}e^{+(C_m\mu_m L_m)}e^{+(G)}\quad\text{Eqn. 4}$$

The subscript legend is, as follows: w=water; L=lipid; and m=melanin. After calibration is performed, the required light-emitting diode (LED) inputs can then be used to perform hydration level measurements. As can be seen from the next equation (i.e., Eqn. 8), contribution from static components (e.g., melanin and lipid absorption), as well as tissue scattering effects G, can be cancelled out, while differential water concentration can be reported and/or determined from the slope:

$$I_{out} = I_{out,equal} e^{-(\mu_w(w-w_0)L)} e^{+(c_m\mu_m L_m)} e^{-(c_m\mu_m L_m)} e^{+(c_L\mu_L L_L)} e^{-(c_L\mu_L L_L)} e^{+(G)} e^{-(G)} \qquad \text{Eqn. 5}$$

(with cancellation strikethroughs on the last four exponential terms)

The slope can be derived from a plot of the following equation (Eqn. 6), as the slope (i.e., $-(w-w_0)L$) thereof providing a differential water concentration:

$$\text{Ln}(I_{out}) = -\mu_w(w-w_o)L + \text{Ln}(I_{out,equal}) \qquad \text{Eqn. 6}$$

If the value for the path length L is not expressly factored out, the slope can be considered proportional to the difference between the current water concentration (w) and the initial water concentration ($w_0$). It is to be understood that having the slope be proportional to the differential water concentration may be sufficient for the purposes of the present method as a way of tracking relative levels and/or changes in water concentration in tissues of a given human body part H (i.e., in part, because the water concentration is a fraction of unity—that is, the concentration is a proportion to begin with and not an actual water amount). If desired, the total change of slope can be calibrated against the total water loss (e.g., weight in pounds; mass in kilograms; etc.) during, for example, a given workout or run.

Figure 8:
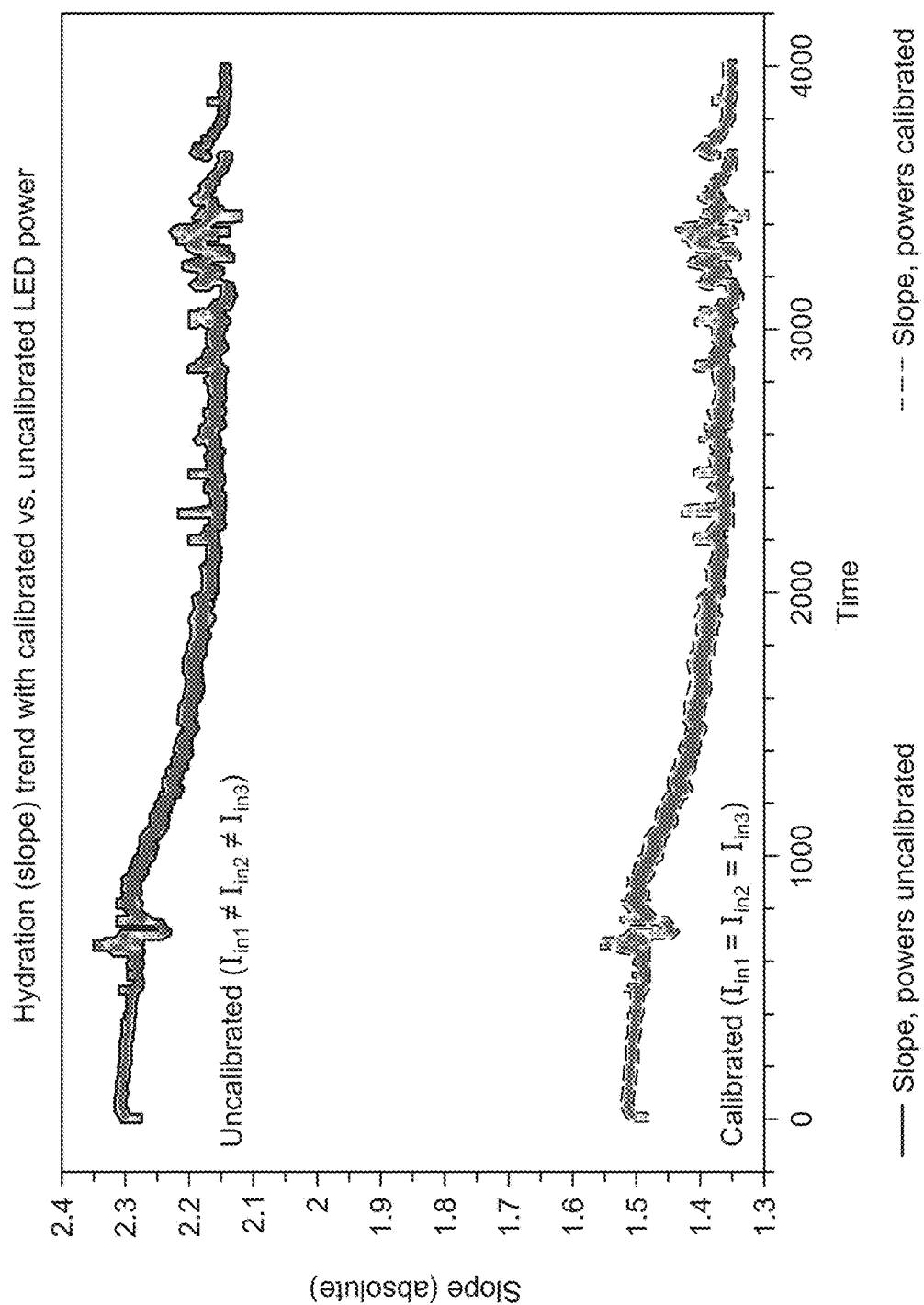
FIG. 8 is a plot of the slope associated with a transmitted intensity versus water absorption coefficient over time, comparing a situation in which the respective LED (light emitting diode) powers are calibrated to a situation in which the respective LED powers are not calibrated, in accordance with an example implementation of the present disclosure.

In another example, the trend of body hydration may be determined with the light-emitting diode 120, 130 (FIGS. 1A, 1B, and 1C) input power ($I_{in}$) requirement removed, as illustrated in FIG. 8. When the input power ($I_{in}$) requirement is removed (i.e., the input powers of the light-emitting diodes 120, 130 (FIGS. 1A, 1B, and 1C) are no longer in known ratios "R" of one another) and the powers of the light-emitting diodes 120, 130 are in unknown and/or uncalibrated ratios, the slope can have a additional direct current (DC) offset term that is proportional to the mismatch of the input powers ($I_{in}$). In an embodiment employing a two-wavelength configuration (e.g., a hydration monitor 110 employing a light-emitting diode module 124 having two (2) light-emitting diodes 120 as shown in FIG. 1B), the DC offset can be expressed as:

$$\text{Slope} = -CL + DC_{offset} \qquad \text{Eqn. 7a}$$

$$DC_{offset} = \frac{\text{Ln}(I_{in2}) - \text{Ln}(I_{in1})}{\mu_{a,2} - \mu_{a,1}} \qquad \text{Eqn. 7b}$$

Figure 6A:
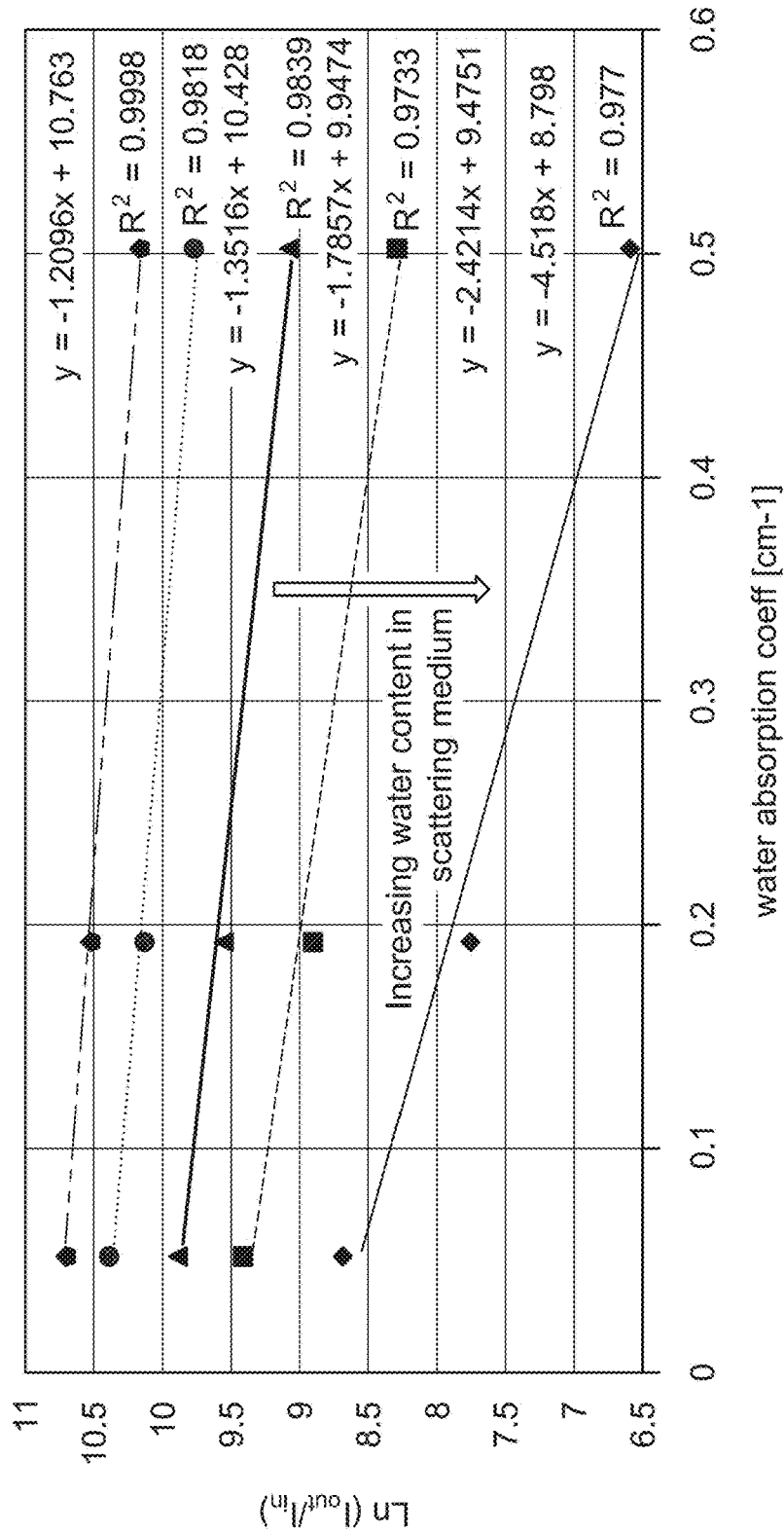
FIG. 6A is a graph measuring transmitted intensity versus water absorption coefficient, relative to increasing water content in a scattering medium, using three wavelengths for plotting, in accordance with an example implementation of the present disclosure.

FIG. 6A illustrates a validation of the example first method, in which the water content was measured in controlled samples, each sample having an increasing water content in a scattering medium. The scattering medium used, per the validation test, has similar optical properties as human tissues. The data were collected using light having three (3) different wavelengths (data collected for light having wavelengths 880 nm, 940 nm, and 970 nm is illustrated, although it is to be understood that light having other wavelengths can be used) using three (3) distinct light-emitting diodes (such as the light-emitting diodes 120 shown in FIG. 1A). As the water content increased: (1) the slope becomes more negative, corresponding to a larger concentration C; and (2) the overall intensity of ($I_{out}/I_{in}$) is lower given the stronger absorption of signal by the water, resulting in a lower $I_{out}$ and thus a decreasing y-intercept.

Figure 6B:
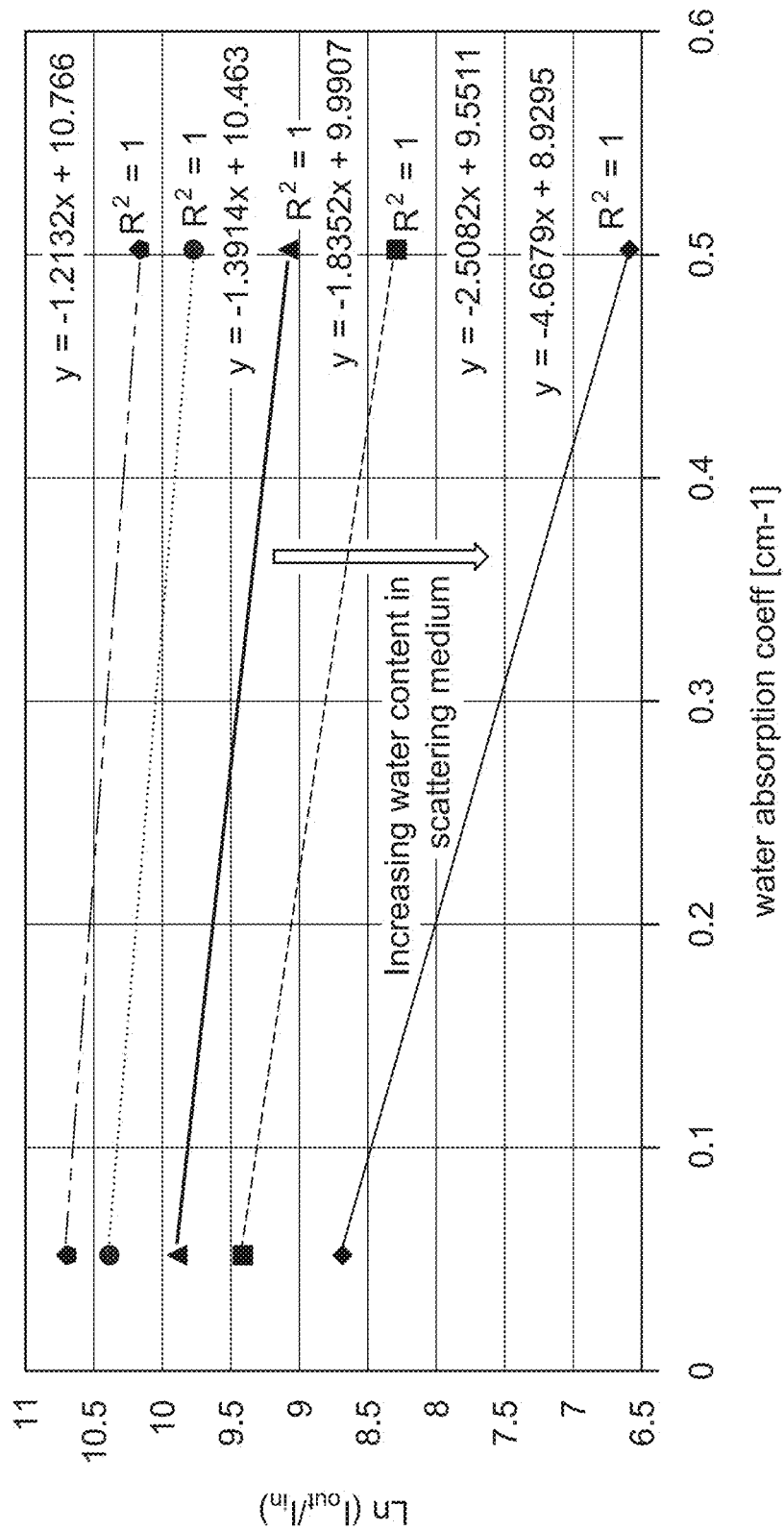
FIG. 6B is a graph measuring transmitted intensity versus water absorption coefficient, relative to increasing water content in a scattering medium, using two wavelengths for plotting, in accordance with an example implementation of the present disclosure.

FIG. 6B illustrates a variation of the example first method, in which light having only two (2) wavelengths of the same data set is used (data collected for light having wavelengths 880 nm and 970 nm is illustrated, although it is to be understood that light having other wavelengths can be used). Thus, for example, a hydration monitor 110 employing a light-emitting diode module 124 having two (2) light-emitting diodes 120 as shown in FIG. 1B may be used. Consequently, upon confirming a high level of correlation to water concentration in the proof-of-concept stage using light of three wavelengths, further implementation may be provided, for example, using light of only two wavelengths. Removing one wavelength and its corresponding light-emitting diode has the advantage of saving cost and area on the product (e.g., device 100 and/or hydration monitor 110). It is to be noted that aspects of the slope method for a two-wavelength arrangement function in the same manner as the three-wavelength arrangement, with the only difference that the value of "R squared" for a two (2) point fit is always one and can no longer be used as a "quality of fit" parameter. However, the "quality of fit" parameter may be optional in a final implementation, particularly if confirmed at a prototype stage using three (3) points.

Figure 7A:
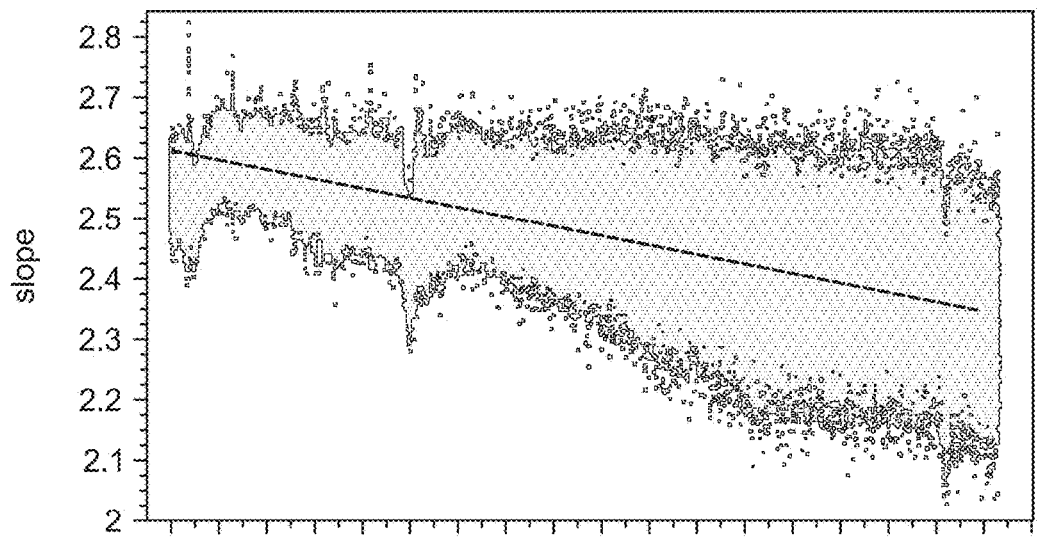
FIG. 7A is a plot of the slope associated with a transmitted intensity versus water absorption coefficient, as determined while monitoring a hydration level of a running athlete during a 1.5 hour run, in accordance with an example implementation of the present disclosure.
Figure 7B:
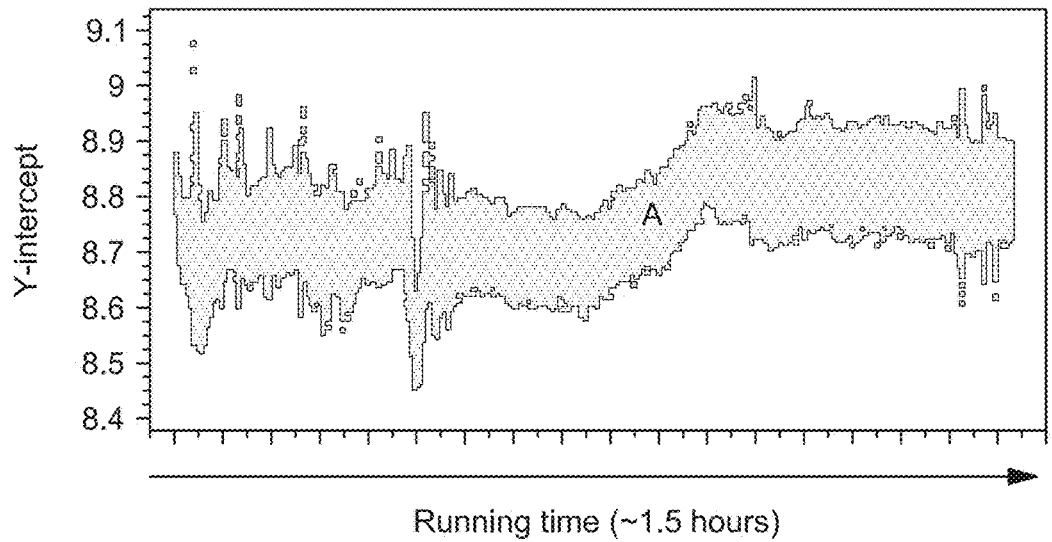
FIG. 7B is a plot of the Y-intercept associated with transmitted intensity versus water absorption coefficient, as determined during monitoring of the hydration level of a running athlete during a 1.5-hour run, as set forth in FIG. 7A.

FIGS. 7A and 7B plot the slope and y-intercept, respectively, over time, while monitoring a hydration level of a running athlete, using the first example method. FIG. 7A illustrates monitoring of dehydration of a running athlete employing the device 100 and/or hydration monitor 110 during a 1.5 hour run. The decrease in body hydration level is indicated by a linear drop of slope value. The total change of slope can, in some embodiments, be calibrated against total water loss (e.g., in weight or mass, such as kg or lbs.) during the run. The y-intercept plot of FIG. 7B captures sudden changes (e.g., due to motion and/or coupling between the light sensor and the body) in signal (e.g., output intensity) common to all three different wavelengths (e.g., point A). As can be seen, the change corresponding to point A does not occur in the slope data, thereby providing a hydration level that is less susceptible to such changes. If, however, the change in signal affects the three (3) wavelengths of light to a different extent, then the residue difference can still be discerned in the slope and affect the reported water concentration. The comparative plots of slope and y-intercept over time help illustrate the value of the present method, given that, over time, it can be seen that, on the whole, the slope value is not tied to changes in the y-intercept.

Given that a purpose of the techniques implemented by the device 100 as disclosed herein is to report the trend of body hydration, i.e., the trend of the slope over time, and that the DC offset has no impact on the trend, the slope method can work properly with the input requirement being removed.

As previously discussed, when a hydration sensor such as the hydration monitor 110 is worn on a human body, the overall detected signal depends not only on the absorption of body water, but also absorption of other tissue constituents such as lipid and melanin. While body water is a dynamic component that changes over time during a workout, the other components are static. Across a diverse population, lipid and melanin contents do vary. Hence the static tissue absorption baseline due to lipid and melanin can also be expected to vary.

However, similar to where the powers of the light-emitting diodes 120, 130 are not known and/or are not calibrated, the effect of different static tissue absorption can be captured in a manner equivalent to having the input powers of the light-emitting diodes 120, 130 being different, while treating the tissue absorption as the same. For example, two different users may have two different lipid contents, $C_{high}$ and $C_{low}$. The user with high lipid content can expect to see a lower detected signal at 940 nm due to the stronger absorption based on lipids at this wavelength. The situation is generally equivalent to this user having lower input light-emitting diode power at 940 nm compared to the other user, while the lipid composition is treated to be the same as the other user.

Figure 9A:
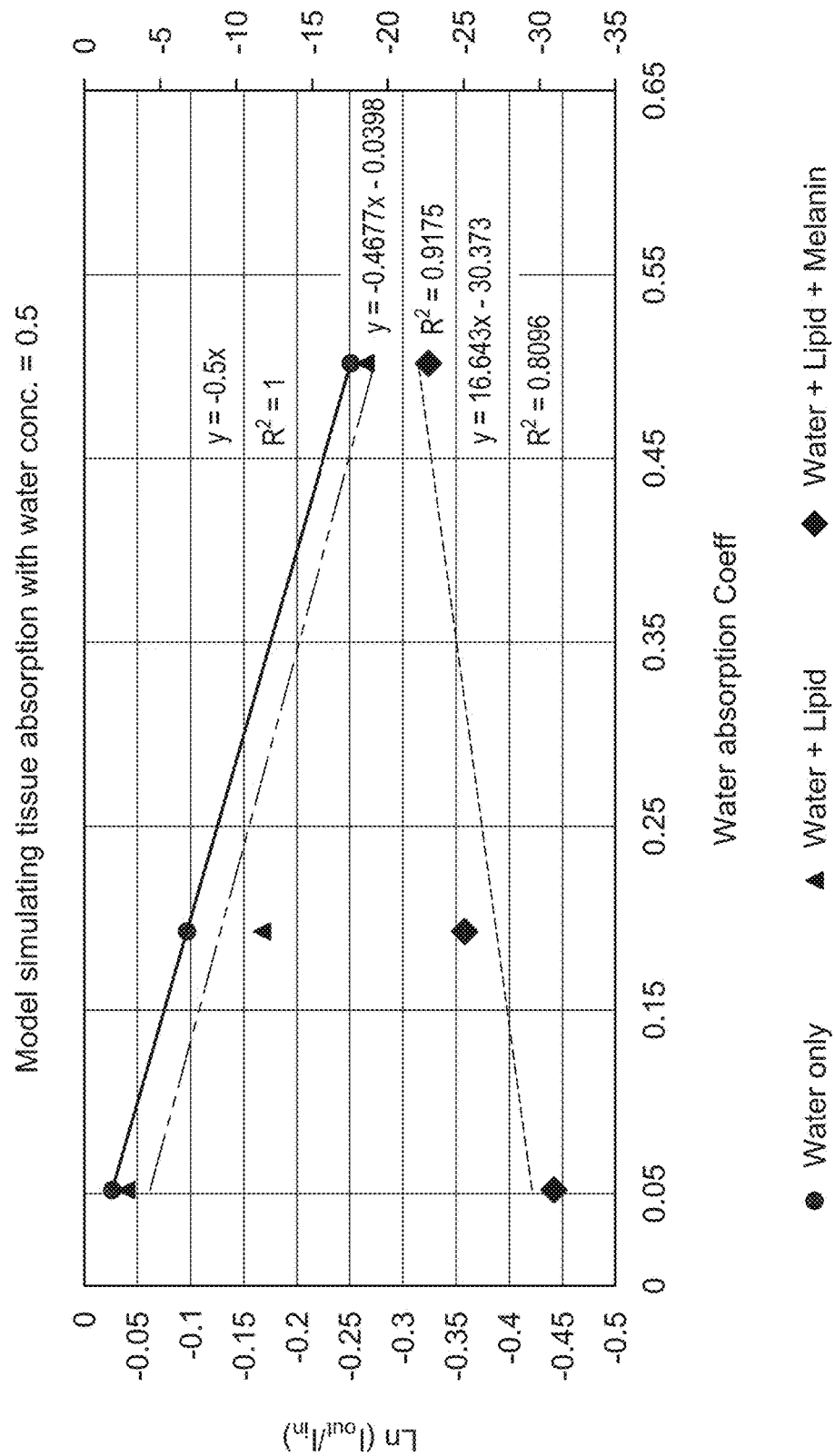
FIGS. 9A and 9B are a series of graphs simulating tissue absorption, respectively accounting for water only, water and lipids, and water, lipids, and melanin, plotting transmitted intensity versus water absorption coefficient, relative to increasing water content in a scattering medium, in accordance with an example implementation of the present disclosure.
Figure 9B:
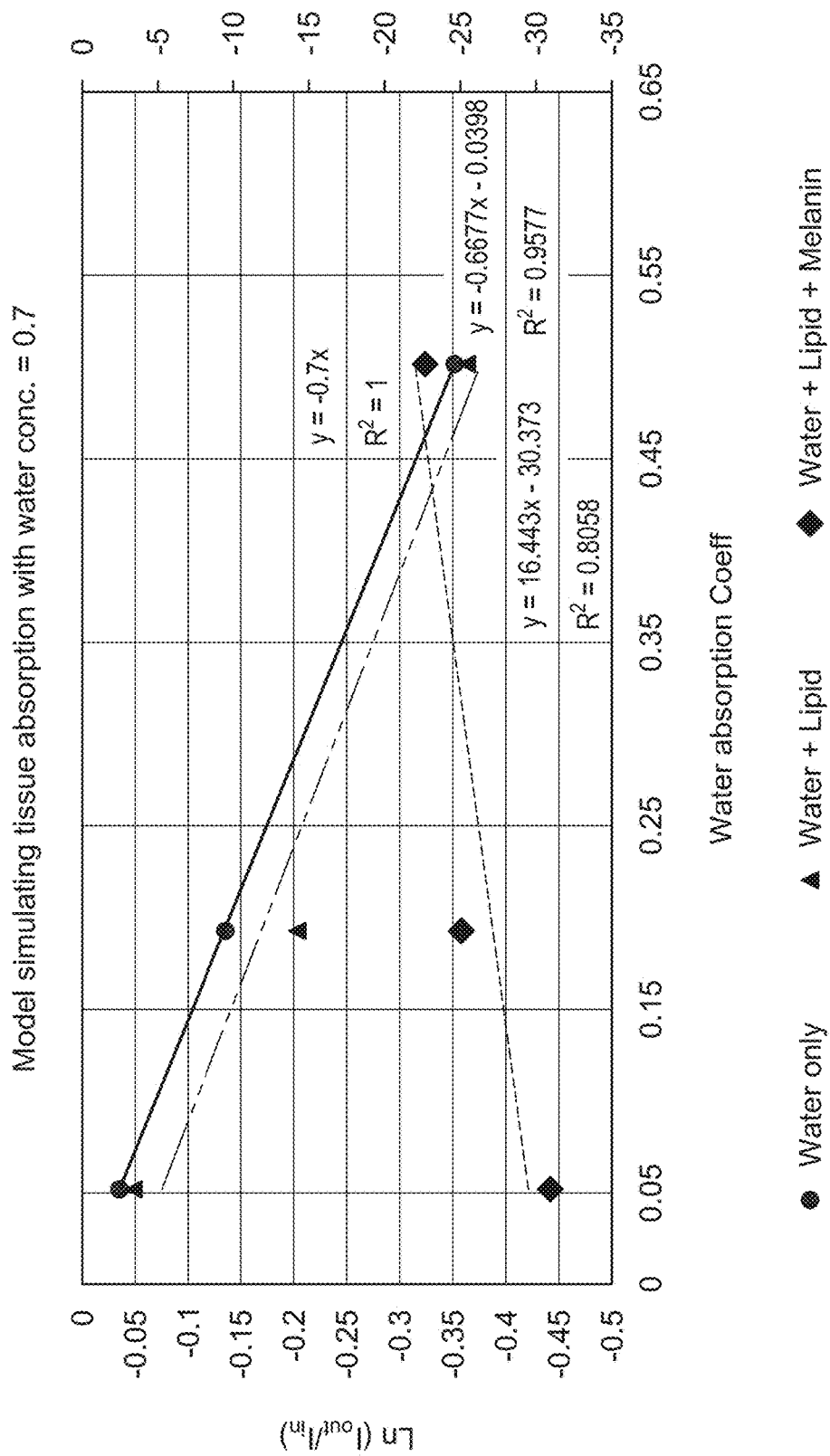

The implication from the scenario where the powers of the light-emitting diodes 120, 130 are not known and/or calibrated indicates that the trend of the slope can be expected to be the same or similar regardless of the different static tissue composition. This scenario can be expected because different static tissue absorption is equivalent to using light-emitting diodes 120, 130 having different input powers $I_{in}$. The difference results in a DC offset in the slope value, with no impact on the body hydration trend (slope trend). Consequently, the slope method can be applied to a diverse population with different tissue composition to detect a hydration trend, and, per such an embodiment, it is possible to forego an adjustment/correction for such a difference in tissue composition and still determine a hydration trend. FIGS. 9A and 9B, along with Table 1, illustrate this feature. As indicated by Table 1, there is an identical change in slope regardless of the static tissue composition.

Figure 10:
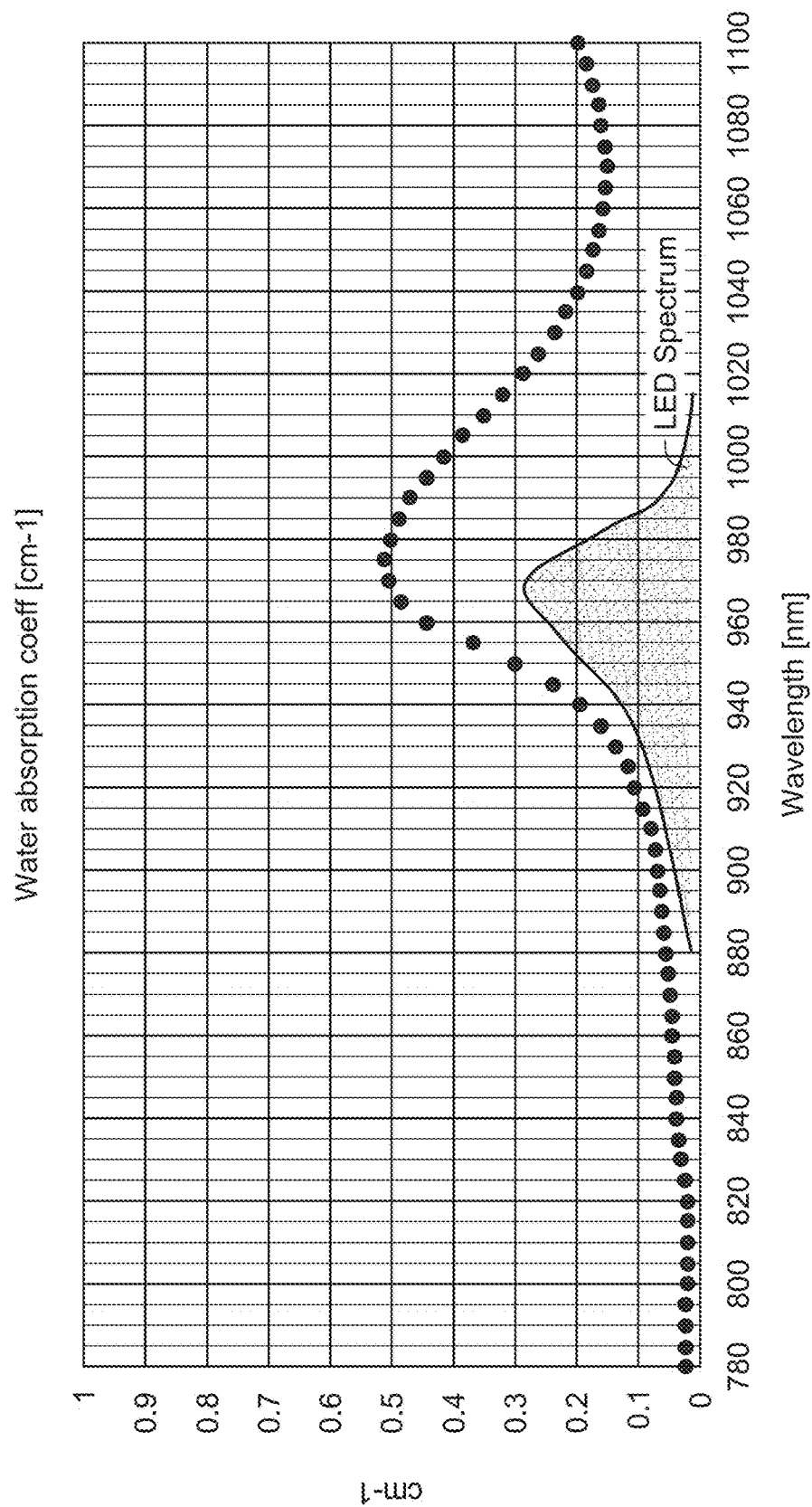
FIG. 10 is a graph illustrating the water absorption coefficient for a light-emitting diode over the bandwidth of wavelengths produced by the light-emitting diode, in accordance with an example implementation of the present disclosure.

In an example embodiment, the accuracy of the slope fitting can be increased. As can be seen from FIG. 5, the x-axis of the slope method corresponds to water absorption coefficient, with units of $cm^{-1}$, where cm is the abbreviation for centimeters, at the incident wavelength of each light-emitting diode. However as seen from FIG. 10, a light-emitting diode is not a monochromatic source (single wavelength) but has a typical bandwidth of +/−15 nm. If the absorption coefficient value was taken from a look-up table at the nominal wavelength, this will result in error in the linear regression fitting.

TABLE 1

| Tissue composition | Slope value | | |
|---|---|---|---|
| | Water Conc. = 0.5 | Water Conc. = 0.7 | D Slope |
| Water only | −0.5 | −0.7 | 0.2 |
| Water + Lipid | −0.47 | −0.67 | 0.2 |
| Water + Lipid + Melanin | 16.6 | 16.4 | 0.2 |

However, a more accurate fitting of slope can be achieved if plotted against an effective water absorption coefficient, obtained by integrating the absorption coefficient $\mu_a(\lambda)$ with the light-emitting diode spectrum $S_{LED}(\lambda)$:

$$\mu_{a,effective} = \frac{\int S_{LED}(\lambda)\mu_a(\lambda)d\lambda}{\int S_{LED}(\lambda)d\lambda} \quad \text{Eqn. 8}$$

Figure 11A:
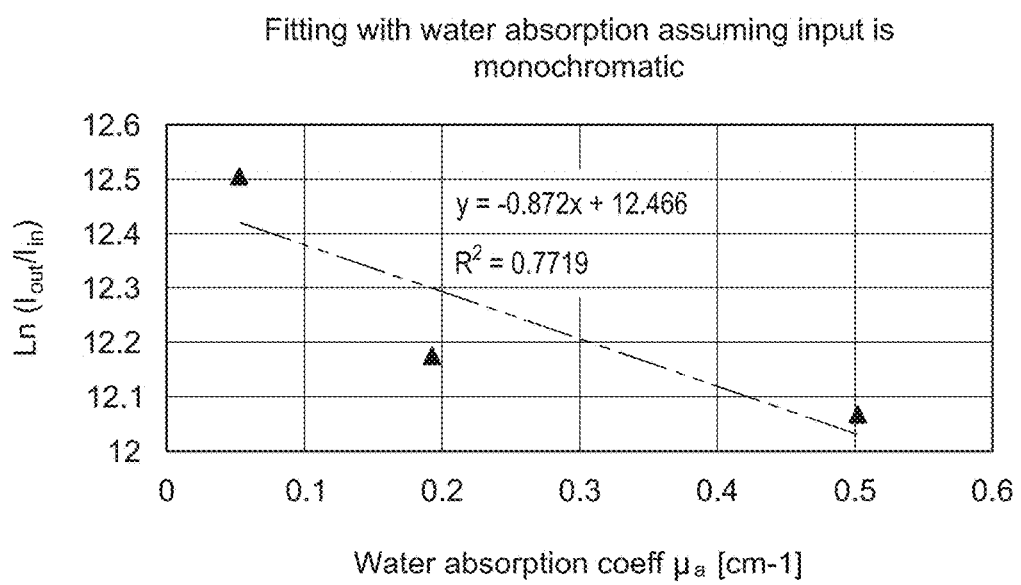
FIG. 11A is a graph of transmitted intensity versus an effective water absorption coefficient obtained by assuming the light-emitting diode is monochromatic, in accordance with an example implementation of the present disclosure.
Figure 11B:
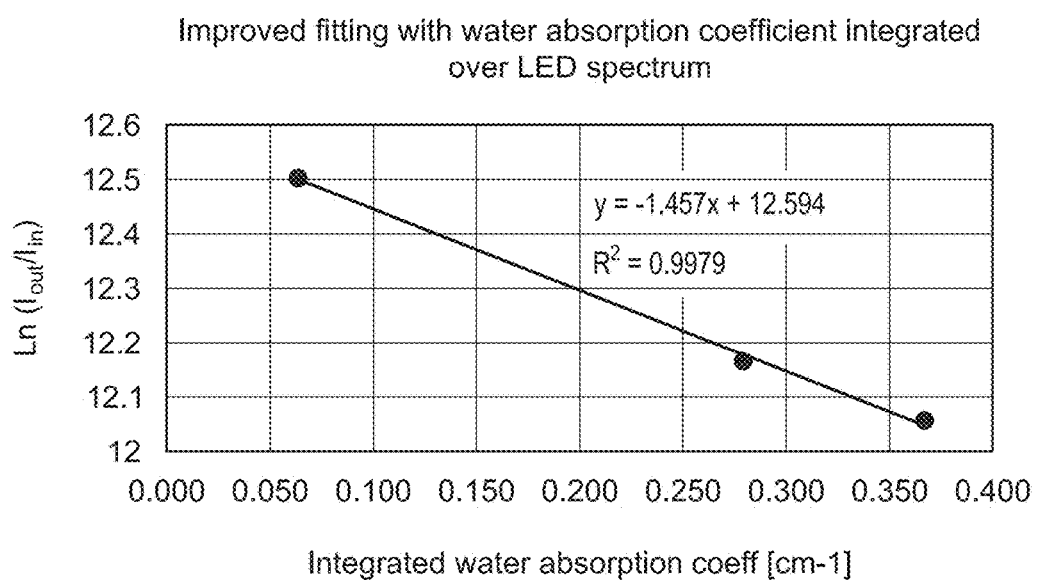
FIG. 11B is a graph of transmitted intensity versus an effective water absorption coefficient obtained by integrating the absorption coefficient with the light-emitting diode spectrum, per FIG. 10, in accordance with an example implementation of the present disclosure.

The improvement in fitting of the slope is illustrated in FIGS. 11A and 11B, where the y-axis is plotted using Ln(Iout/Iin) as before (FIG. 11A), and x-axis is now plotted using $\mu_{a,effective}$ instead of $\mu_a$ (FIG. 11B).

Turning now to FIGS. 12A, 12B, 12C, 12D, and 13, the device 100 and method 200 disclosed herein may, in embodiments, employ multiple channels ("CH") to correct for electrical drift and optical motion noise. As utilized herein, different channels are characterized by different path lengths L between the light-emitting diodes 120, 130 and a respective light sensor 116. Thus, a given "channel" is associated with the path length L between respective light-emitting diode modules 114, 124, 134 and light sensors 116, as shown in FIG. 1D. Moreover, two light-emitting diodes 120, 130 emitting light having two different wavelengths comprise a single channel if the path lengths L between the light-emitting diodes 120, 130 and the photodiode 116 are the same, for example, when the light-emitting diodes 120, 130 are part of a common light-emitting diode module 114, 124, 134 and the light travels along a path to a common light sensor 116.

Figure 12A:
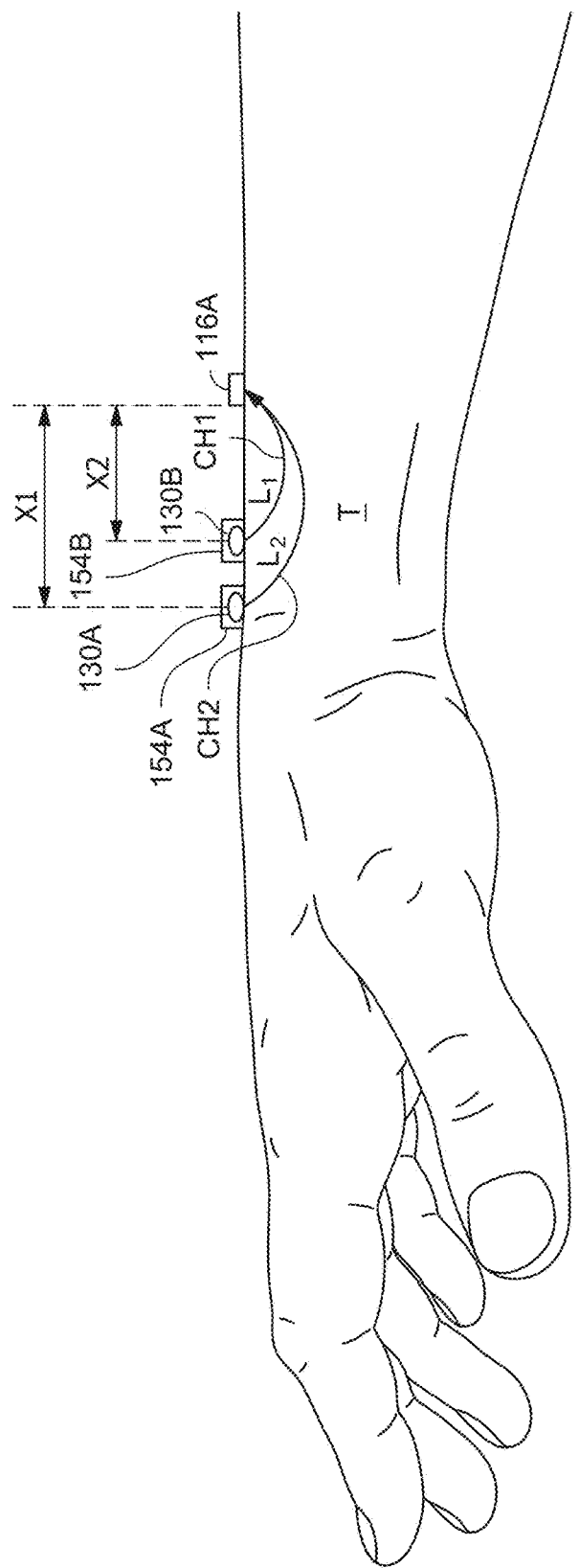
FIGS. 12A and 12B are side, diagrammatic views of example hydration monitors employing a multiple-channel configuration, in accordance with an example implementation of the present disclosure.
Figure 12B:
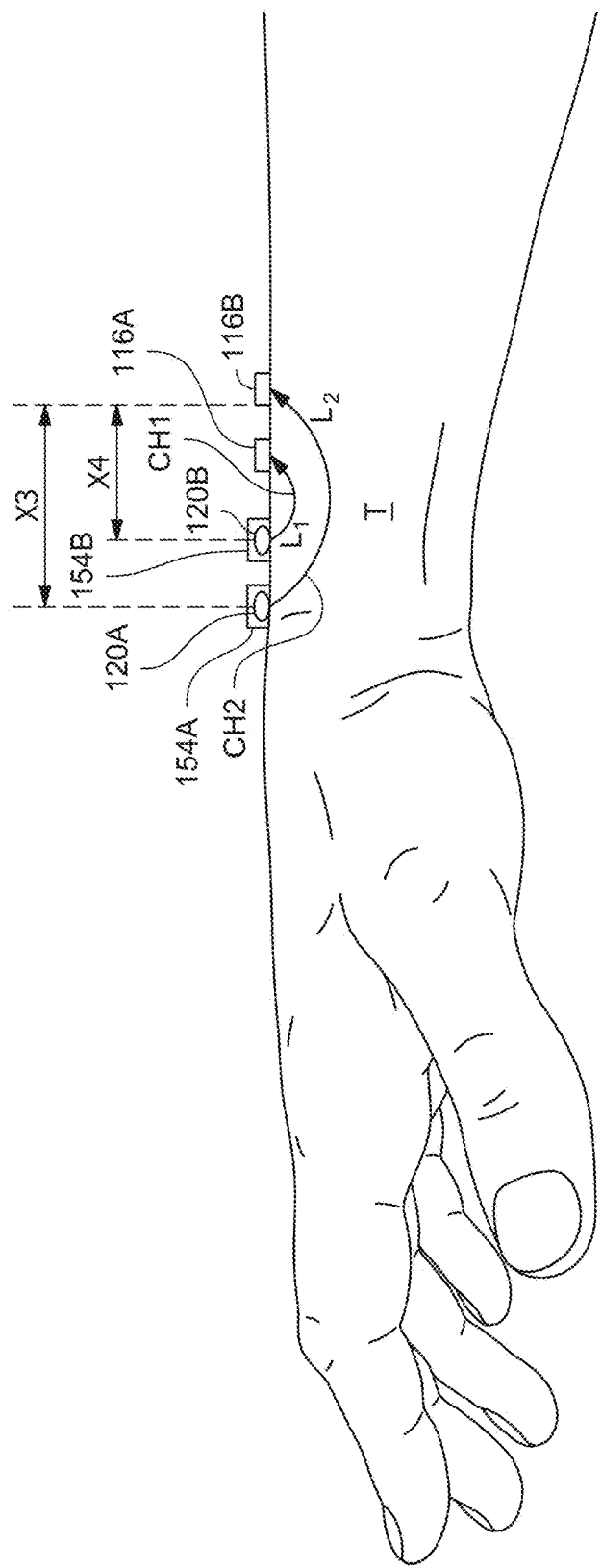

As illustrated in FIGS. 12A and 12B, multiple sets of light-emitting diodes 120A, 120B and photodiodes 116A, 116B are provided to collect signals from multiple channels. In FIGS. 12A and 12B, dual channel configurations are shown wherein two channels CH1, CH2 are furnished, each corresponding to different path lengths $L_1$, $L_2$, respectively. Two different examples of dual channel configurations are illustrated. In FIG. 12A, a dual channel configuration is shown having two light-emitting diode modules 154A and 154B and one light sensor (e.g., photodetector) 116A creating two separate path lengths $L_1$, $L_2$ and thus two distinct channels CH1 and CH2, respectively. In FIG. 12B, a dual channel configuration is shown having two light-emitting diode modules 154A and 154B and two light sensors (e.g., photodetectors) 116A and 116B. This configuration also creates two separate path lengths $L_1$, $L_2$ and respective channels CH1 and CH2. Separation distances between the light-emitting diode modules 154A and 154B and the light sensor 116A are denoted as X1 and X2, respectively, where X1>X2 (e.g., X1=1 cm). As will be described below in reference to FIGS. 12C-12E, the two light-emitting diode modules 154A and 154B and the two light sensors 116A and 116B depicted in FIG. 12B may also be used to implement four distinct channels (e.g., CH1-CH4). Separation distances between the light-emitting diode modules 154A and 154B and the light sensor 116B are denoted as X3 and X4, respectively, where X3>X4.

Figure 12C:
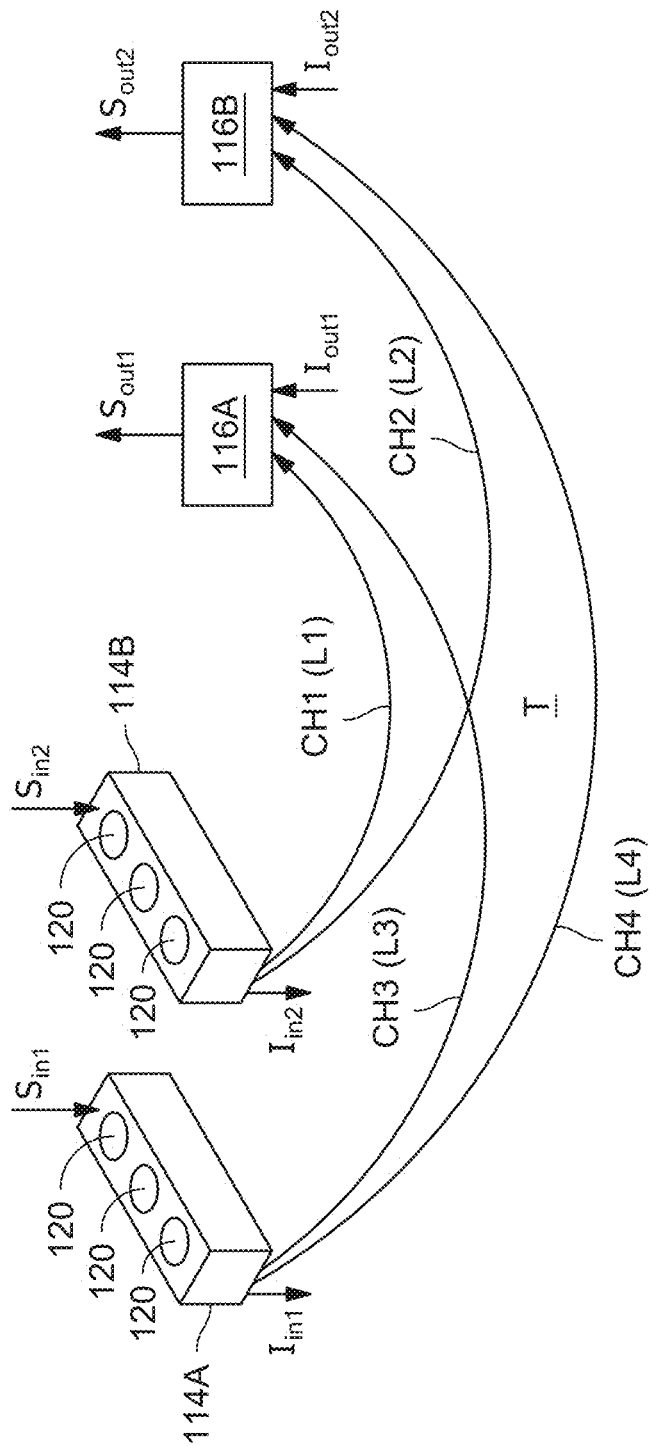
FIGS. 12C, 12D, and 12E are perspective, diagrammatic views illustrating example multiple-channel configurations in accordance with an example implementation of the present disclosure.
Figure 12D:
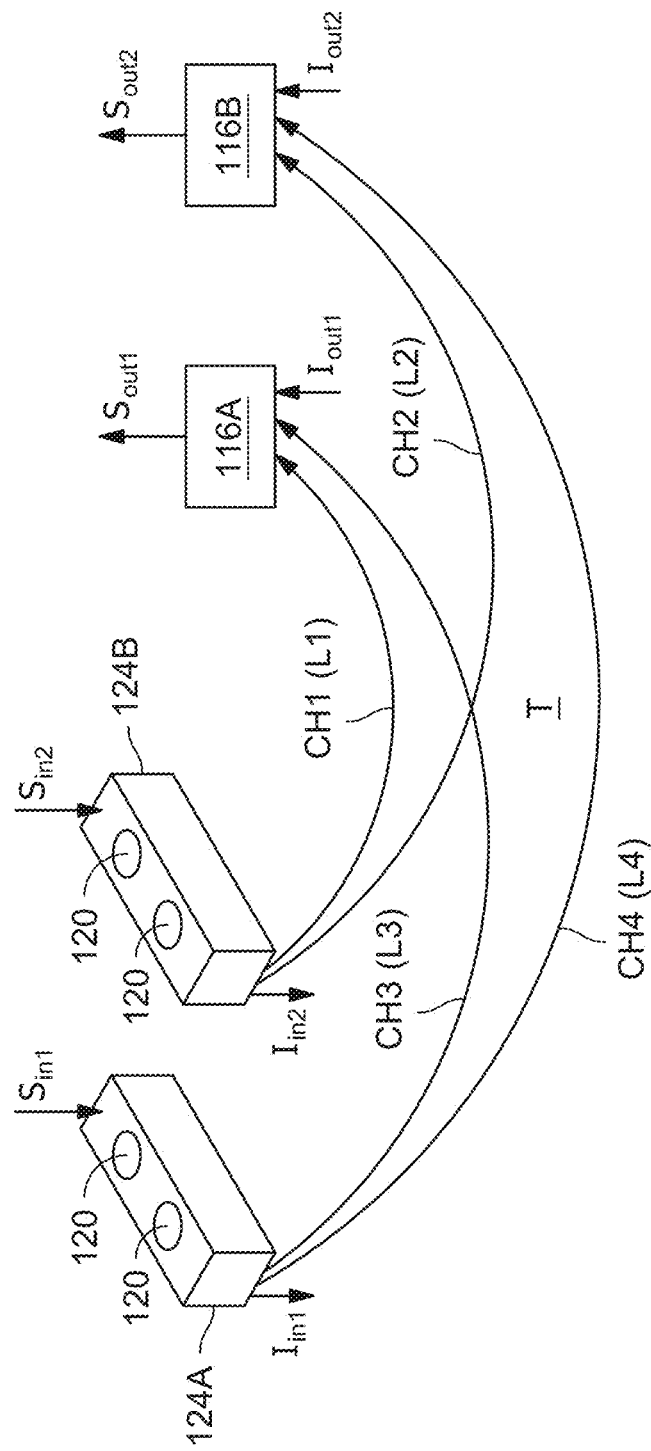
Figure 12E:
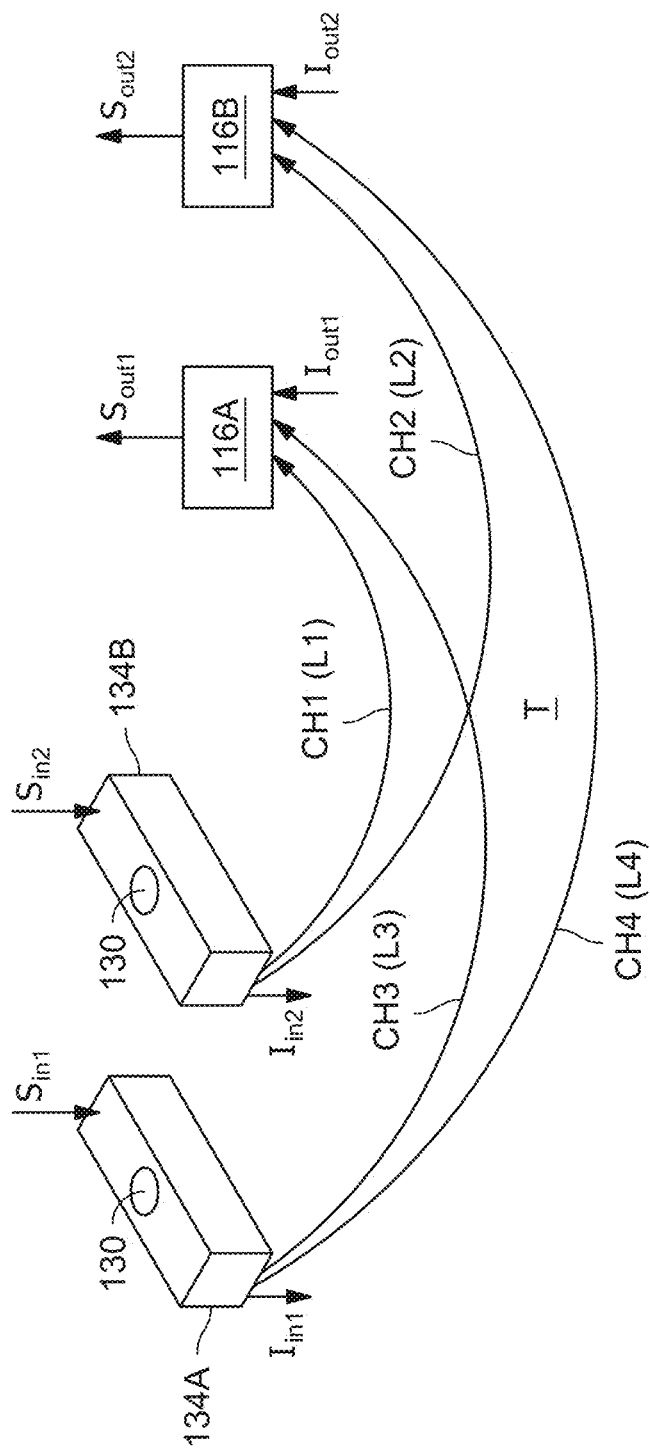

FIGS. 12C, 12D, and 12E illustrate operation of the hydration monitors 110 shown in FIGS. 1A, 1B, 1C, and 1D in accordance with the Beer-Lambert law. In FIGS. 12C, 12D, and 12E, dual channel configuration are shown having two light-emitting diode modules (114A and 124B in FIG. 12C, 124A and 124B in FIG. 12D, and 134A and 134B in FIG. 12E, respectively) and two light sensors (e.g., photodetectors) 116A and 116B. These configurations create multiple separate path lengths $L_1$, $L_2$, $L_3$, and $L_4$ and respective channels CH1, CH2, CH3 and CH4. The Beer-Lambert law (Eqn. 1) relates the transmitted intensities $I_{out1}$, $I_{out2}$ which is detected by the light sensors 116A and 116B of channels CH1 and CH2, respectively, to produce an output signals $S_{out1}$, $S_{out2}$, respectively, to the incident intensity $I_{in1}$, $I_{in2}$ transmitted into the tissue T by the light-emitting diodes 120, 130 in response to the input signals $S_{in2}$, $S_{in2}$. By taking ratios of the detected powers from the channels (found using Eqns. 9A and 9B), the differential signal corresponding to the incremental volume can be extracted. Hydration slope can then be obtained by a linear fit of the differential signal against the water absorption coefficient.

$$I_{CH1} = I_1 e^{-\mu CL_1} A_1 \qquad \text{Eqn. 9a}$$

$$I_{CH2} = I_2 e^{-\mu CL_2} A_2 \qquad \text{Eqn. 9b}$$

where $I_{ch1}$ corresponds to $I_{out1}$, $I_{ch2}$ corresponds to $I_{out2}$, $I_1$ corresponds to $I_{in1}$, and $I_2$ corresponds to $I_{in2}$.

The corrected signal can be expressed, as follows:

$$\frac{I_{CH2}}{I_{CH1}} = \frac{I_2}{I_1}\frac{A_2}{A_1} e^{-\mu C(L_2-L_1)} \qquad \text{Eqn. 10}$$

where L is the path length and $A_1$ and $A_2$ are the photodiode responses for each channel, respectively.

Figure 13:
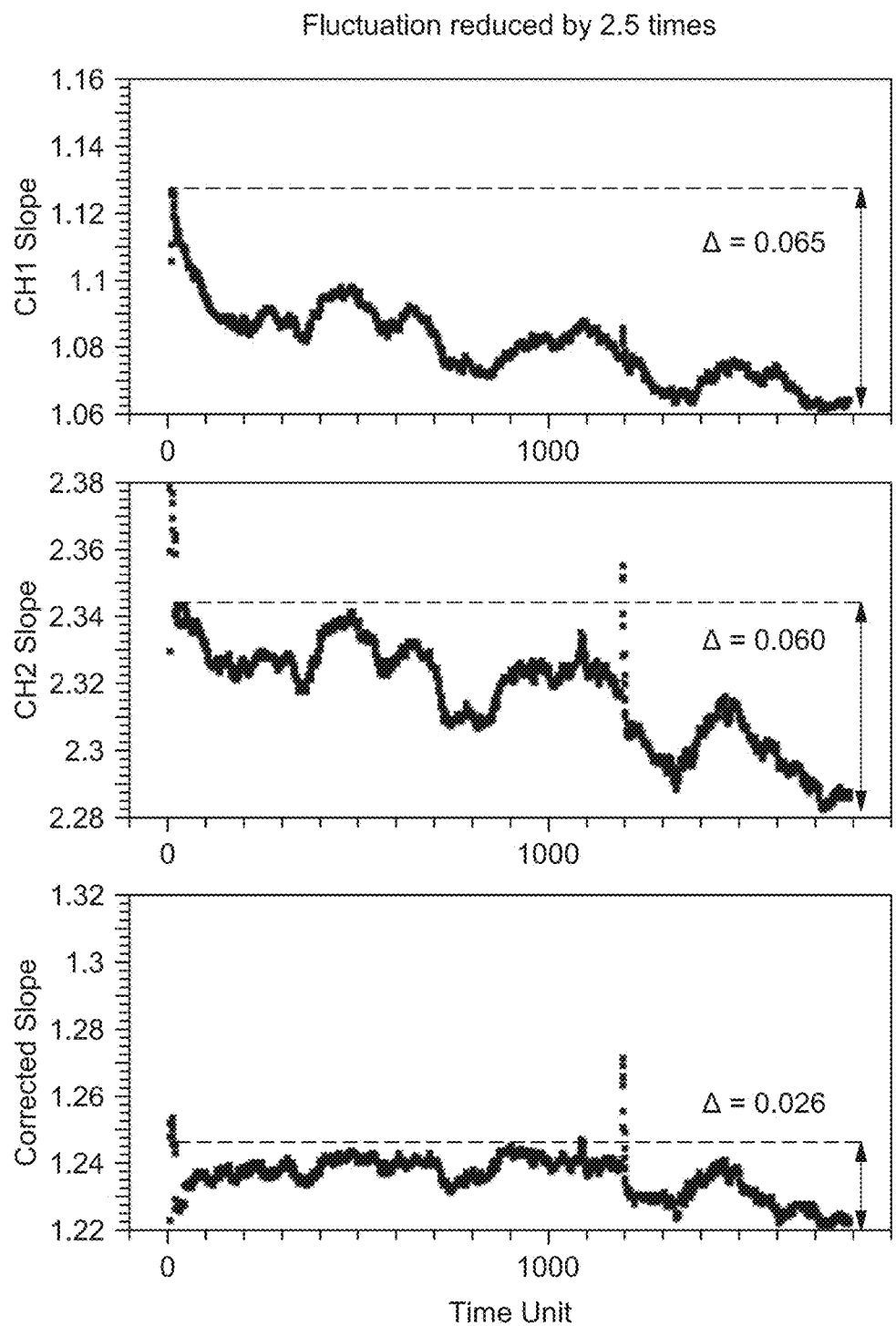
FIG. 13 is a series of plots of the hydration slope generated using the example hydration modules shown in FIGS. 12A and 12B over a period of time.

Noise (e.g., electrical drift, motion noise) that is common to the path lengths L can be eliminated or reduced as a result, as can be seen from FIG. 13. It is noted that, when using this corrective method, full correction is achieved by matching the powers of the light-emitting diodes 120, 130 ($I_1=I_2$), photodiode response ($A_1=A_2$), and/or electronic gain response for the channels involved.

It is to be understood that the present application is defined by the appended claims. Although embodiments of the present application have been illustrated and described herein, it is apparent that various modifications may be made by those skilled in the art without departing from the scope and spirit of this disclosure.

What is claimed is:

1. A device, comprising:
 a controller;
 a memory coupled to the controller;
 a light-emitting diode (LED) module coupled to the controller and including a first LED and a second LED;
 a light sensor coupled to the controller; and
 the first LED configured to receive a first input signal from the controller and to emit a first wavelength of light having a first incident intensity into tissue,
 the second LED configured to receive a second input signal from the controller and to emit a second wavelength of light having a second incident intensity into the tissue,
 the first wavelength of light being different than the second wavelength of light,
 the light sensor being configured to generate a first output signal indicative of a first transmitted light intensity in the tissue associated with the first incident intensity, and a second output signal indicative of a second transmitted light intensity in the tissue associated with the second incident intensity,
 the controller being configured to:
 receive the first output signal and the second output signal,
 access the memory to retrieve data representing a first water absorption coefficient associated with the first wavelength and data representing a second water absorption coefficient associated with the second wavelength, and
 calculate, based on the first transmitted light intensity versus the first water absorption coefficient and the second transmitted light intensity versus the second water absorption coefficient, data representing water content in the tissue.

2. The device of claim 1 and further comprising:
 a substrate, the LED module and the a light sensor are disposed on the substrate and are spaced apart from each other by a separation distance.

3. The device of claim 1, wherein the first incident intensity is different than the second incident intensity.

4. The device of claim 1, wherein the first incident intensity is substantially equal to the second incident intensity.

5. The device of claim 1, wherein the data representing water content in the tissue is calculated by a linear regression of the first transmitted light intensity versus the first water absorption coefficient and the second transmitted light intensity versus the second water absorption coefficient.

6. The device of claim 5, wherein the data representing water content in the tissue comprises a slope indicative of an absolute water content in the tissue.

7. The device of claim 5, wherein the data representing water content in the tissue comprises a trend of slope indicative of a trend in water content in the tissue.

8. The device of claim 1, wherein the first LED and the second LED comprise broadband LED's.

9. The device of claim 1, wherein the first wavelength of light and the second wavelength of light comprise infrared light.

10. The device of claim 1, wherein the first wavelength of light and the second wavelength of light comprise broadband infrared light.

11. A device, comprising:
 a controller;
 a memory coupled to the controller;
 a light module coupled to the controller and including a first light source and a second light source;
 a light sensor coupled to the controller; and
 the first light source configured to receive a first input signal from the controller and to emit a first wavelength of light having a first incident intensity into tissue,
 the second light source configured to receive a second input signal from the controller and to emit a second wavelength of light having a second incident intensity into the tissue,
 the first wavelength of light being different than the second wavelength of light,
 the light sensor being configured to generate a first output signal indicative of a first transmitted light intensity in the tissue associated with the first incident intensity, and a second output signal indicative of a second transmitted light intensity in the tissue associated with the second incident intensity,
 the controller being configured to:
 receive the first output signal and the second output signal,
 access the memory to retrieve data representing a first water absorption coefficient associated with the first wavelength and data representing a second water absorption coefficient associated with the second wavelength, and
 calculate a linear regression of the first transmitted light intensity versus the first water absorption coefficient and the second transmitted light intensity versus the second water absorption coefficient to generate data representing a slope indicative of water content in the tissue.

12. The device of claim 11, wherein the first light source and the second light source comprise broadband light-emitting diodes.

13. The device of claim 11, wherein the first light source and the second light source comprise light-emitting diodes.

14. The device of claim 11 and further comprising:
a substrate, the light module and the a light sensor are disposed on the substrate and are spaced apart from each other by a separation distance.

15. The device of claim 14, wherein the separation distance is substantially 1 centimeter or less.

16. The device of claim 11, wherein the first incident intensity is different than the second incident intensity.

17. The device of claim 11, wherein the first incident intensity is substantially matched with the second incident intensity.

18. The device of claim 11, wherein the first wavelength of light and the second wavelength of light comprise infrared light.

19. The device of claim 11, wherein the first wavelength of light and the second wavelength of light comprise broadband infrared light.

20. The device of claim 11, wherein the controller is configured to generate the first input signal and the second input signal at different times.

* * * * *